United States Patent
Bernard-Capel et al.

(10) Patent No.: US 8,097,411 B2
(45) Date of Patent: Jan. 17, 2012

(54) GENOMIC MARKER FOR TENDERNESS MEAT

(75) Inventors: Carine Bernard-Capel, Nanterre (FR); Isabelle Cassar-Malek, Saint Genes Champanelle (FR); Jean-Francois Hocquette, Beaumont (FR)

(73) Assignees: Institut National de la Recherche Agronomique, Paris (FR); APIS Gene, Paris (FR)

( * ) Notice: Subject to any disclaimer, the term of this patent is extended or adjusted under 35 U.S.C. 154(b) by 149 days.

(21) Appl. No.: 12/310,826

(22) PCT Filed: Sep. 12, 2007

(86) PCT No.: PCT/EP2007/059585
§ 371 (c)(1),
(2), (4) Date: Jun. 2, 2009

(87) PCT Pub. No.: WO2008/031846
PCT Pub. Date: Mar. 20, 2008

(65) Prior Publication Data
US 2009/0311689 A1     Dec. 17, 2009

(30) Foreign Application Priority Data
Sep. 12, 2006 (EP) .................................. 06300943

(51) Int. Cl.
*C12Q 1/68* (2006.01)
*C12P 19/34* (2006.01)
(52) U.S. Cl. ................. 435/6.1; 435/6.11; 435/6.12
(58) Field of Classification Search .......... None
See application file for complete search history.

(56) References Cited

FOREIGN PATENT DOCUMENTS

| | | |
|---|---|---|
| EP | 1394274 | 3/2004 |
| WO | WO-0029615 | 5/2000 |
| WO | WO-03031592 | 4/2003 |

OTHER PUBLICATIONS

Sasaki et al. Animal Genetics, vol. 37, No. 1, Feb. 2006, pp. 40-46.*
Database EMBL [Online], "Bos taurus DnaJ (Hsp40) homolog, subfamily A, member 1 (DNAJA1), mRNA complete cds." XP002426562 retrieved from EBI accession No. EMBL:BT021066 Database Accession No. BT021066 (Feb. 17, 2005).
Bernard et al., "A cDNA macro-array resource for gene expression profiling in ruminant tissues involved in reproduction and production (milk and beef) traits," Journal of Physiology and Pharmacology: An Official Journal of the Polish Physiological Society, vol. 56, Suppl. 3, Jun. 2005, pp. 215-224.

* cited by examiner

*Primary Examiner* — Juliet Switzer
(74) *Attorney, Agent, or Firm* — IM IP Law PLLC; C. Andrew Im

(57) ABSTRACT

The invention concerns the use of a genomic marker comprising a nucleotide sequence corresponding to all or part of the nucleotide sequence SEQ ID No 1, or to all or a part of an allele of the nucleotide sequence SEQ ID No 1 and associated with the phenotype relating to the tenderness of the meat from bovines, for the implementation of any identification method for the quantification of DNAJA1 expression level with the aim of selecting and/or sorting ruminant animals of the bovine type which produce tender meat and/or for the implementation of an identification method of tender meats at the moment of slaughter by direct sampling from the carcass.

The invention concerns identification methods using the real time RT-PCR technique, the hybridization of labelling cDNA with an oligonucleotide probe and the detection of antigen-antibody complexes.

20 Claims, 5 Drawing Sheets

DNAJA1
Bos Taurus :
NM_001015637

```
   1 AACGCTCGGTGAAAGGGGAGGAGGAGCGGGGCGGCTGCCCGAGCTGCGCACAGCAACGCGCTCC
  61 TTCCCGCTCCCCACACGGCATCGGCACCGGCCCCGCCTCACCGGCTGTAAAAATGGTGAAAGAAA
 121 CCACTTACTATGATGTTTGGGGGTCAAACCCAAGAAGAAATGCCACCCAAGAAGAATTGAAAAGG
 181 CTTACAGGAAACTGGCCTTGAAGTACCACCCTGATAAGAATGCAAAGAAATCCAAATGAAGGCGAGAAGT
 241 TTAAACAGATTTCTCAAGCTTACGAAGTGCTCTCTGATGCAAAGAAAAAGGGAGTTATATG
 301 ACAAAGGAGAGAACAGGCAATTAAAGAAGAAGGTGGAGCAGGAGGCAGGATGCACAGAGAGAGAGGTA
 361 TGGACATCTTTGATATGTTTTCGGAGGAGGAGCAGTAACTTAGAAGATTTATATAATGGTGCAACAAGAA
 421 AAAACGTGTCCATCAACTACAGTGTTGTGACAAATGTGAAGGCCGAGGTGGTAAAAAAG
 481 AACTAGCTCTGCAAAGAATGCTGTCCCAATTGCCGAGTTACTGGAATGCAAATAAGAATTCATCAGA
 541 GAGCAGTAGAATGCTGTCCCAATTGCCGAGTTACTGGAATGCAAATAAGAATTCATCAGA
 601 TAGGACCTGGAATGGTTCAGCAAATTCAGTCTGTCTGCATTGAGTGCCATTGTCATGGGG
 661 AGCGGATCACCCCTAAAGATAGATATTCAGTGCAATGCAATGCAAGAAGAAGTTGCGAGAAAA
 721 AGAAAATTCTAGAAGTTCATATTGACAAAGGCATGAAAGATGCCAGAAGATAACATTCC
 781 ATGGTGAAGGAGGACCAGAACCAAGACTGGAGCCGGAGATATTATCATTGTTTAGATC
 841 AGAAGGACCATGCTGTTTACTGCGAGAAGAACCTTTCATGTGTATGGACATAC
 901 AGCTGGTTGAGGCATTGTGTCCTCATCCAGGTCAAATTGTCAAGCATGTGAGATATCAAGTGTGCTAA
 961 TAGTCATCACTTCTCATCCAGGTCAAATTGTCAAGCATGTGAGATATCAAGTGTGCTAA
1021 ATGAAGGCATGCCAATTTATCGTAGGCCAATTTATCGAAAAGGGTCGCCTAATCATTGAATTTA
                                              >>>>>>>>>>>>>>>>>>>>>>>>>>
                                                                   1076
1081 AGGTAAAACTTTCCTGAGAATGGCCTTTCTCTCTCCTGATAAACTCTCTTGCTGGAAAAAC
     >>>>>>>>>>>>>>>>>>************************************
     1057
1141 TTCTGCCTGAGAGGAAGGAAGTAGAAGAGACTGATGAAATGGACCAGGTAGAATTAGTGG
     ******
     1145
1201 ACTTTGATCCAAATCAGGAAAGACGGCCATTACAATGGAGAAGCATACGAGGATGATG
                                                          <<<<<<<<<<<
                                                                 1255
1261 AACATCATCATCCTCGGGTGGTGTTCAGTGTCAGACCTCTTAGTAGGCCTGTGAACAACAC
1321 TCACTGCTGGTGTTTATTGCAGTAGTGATTGAGTGAAGGACTATAATCATATGCTCAC
1381 TACTTGCTTTGTTTGTTTAATATTCAACTATAGTAGTGTTTAAAAGTTAAATGAAGAATAAA
1441 CTCAAATAT
```

Fig. 4

```
  1 TTTCGGAGGGAACATGAAGAGATCCTATTCGTCGCCCGCCCTGGTTGTGTGGGCTCCGTGTTCT
 61 TCCTGCTGTTGCCTGGACCATCCGCGGGCCGATGAGAAGAAGATATAGGCCGGGTGTCATCGGTC
121 TCAAGGTGTACTTTGACCTGCGAATTGGAGATGAAGATATAGGCCGGGTGGTCATCGGTC
                                                     >>>>>>>>>>>
                                                          170
181 TCTTTGGAAAGACTGTTCCAAAAACAGTGGATAATTTGTGGCCTTGGCTACAGGAGAGA
    >>>>>>>>
       189
241 AAGGATTTGGCTACAAAGACAGCAAATTCCATCGTGTGATCAAGGACTTCATGATCCAGG
301 GTGGAGATTTCACCCGGGAGACGGCACTGGAGGTAAGAGCATCTACGGTGAACGCTTCC
                                  <<<<<<<<<<<<<
                                       320
361 CCGATGAGAACTTCAAGCTTAAACACTATGGGCCCGGGTGAGCATGGCCAACGCGG
                          339
421 GCAAAGACACCAACGGCTCCCAGTTCTTCATCACGACAGTCAAGACTGCCTGGCTAGATG
481 GCAAGCACGTAGGTTTCGGCAAAGTTCTAGAGGGCATGGATGTAGTACGGAAGGTAGAGA
541 GCACCAAGACTGACGGTCGGGACAAGAGCCTCTGAAGGACGATCGCAGACTGCGGGCA
601 AGATCGAGGTGGAGAAGCCCTTTGCCATTGCCAAGGAATAGGCCCCAGGACCTCTTCC
661 CTTTGAGCAACTGTCTGTGGCGCTGGCTGTGTGCCCCCAGGGGTGAAGATAGCCGCCACA
721 GGGCTCCGTGCGCGTTTGTAACAAACTCCTACAAACTGACCAATAAAAAAATGGTGT
781 TCCATGGGCCCAGTTTGTAACAAACTCCTACCAACACTGACCAATAAAAAAATGGTGT
841 TTTTTTTAAAAA
```

Fig. 5

GENOMIC MARKER FOR TENDERNESS MEAT

RELATED APPLICATIONS

This application is a §371 application from PCT/EP2007/059585 filed Sep. 12, 2007 which claims priority from European Patent Application No. 06 300 943.5 filed Sep. 12, 2006, each of which is herein incorporated by reference in its entirety.

TECHNICAL FIELD

The invention relates to a genomic marker of a tenderness of a meat of an animal species, in particular of a bovine. The object of the invention is to select and/or to sort populations of bovines as a function of the tenderness of their meat. The invention also has the object of selecting tender meats on the basis of samples of meat taken from carcasses.

BACKGROUND ART

The control of beef quality and more particularly of its sensory characteristics (tenderness, flavor, juiciness and color) is important for beef producers and retailers in order to satisfy consumer's requirements and wishes. Multiple factors control beef sensory quality traits and thus induce great variation in them. It has been shown that meat sensory quality depends not only on production factors such as breed, genotype, age, diet, growth path or slaughter weight (Cassar-Malek I et al., *Animal Science*, 2004; Cuvelier C. et al., *Animal Science*, 2006, Monson F et al., *Meat Science*, 2004; Monson F. et al. *Meat Science*, 2005; Sami A S et al. *Meat Science*, 2004; Sanudo C. et al. *Meat Science*, 2004.), for review, see Geay Y. et al., *Reprod Nutr Dev*, 2001, but also on technical factors (slaughtering conditions, ageing time, cooking process) (Monson F. et al., *Meat Science*, 2004; Monson F. et al., *Meat Science*, 2005).

Genetic and rearing factors are known to affect biological characteristics of muscles (fiber type, collagen, intramuscular adipose tissue, protease activities) which in turn regulate tenderness and flavor. Tenderness has two major components: the background toughness which results from the connective tissue characteristics (mainly collagen content and solubility) and the myofibrillar component closely related to the muscle fiber characteristics (Klont R E et al., *Meat Science*, 1998) which control the tenderization phase characterized by post-mortem proteolysis, a major biological process involved in the conversion of muscle into meat (Koohmaraie M. et al., *Meat Science*, 2002; Veiseth E. et al., *Indicators of milk and beef quality, EAAP Publication* 112, Wageningen Academic Publishers, Wageningen, The Netherlands, 2005). The intramuscular fat and its fatty acids composition determine meat flavor, and lipid oxidation is responsible for odors usually described as rancid (Campo M M. et al., *Meat Science*, 2006, Wood J D et al., *Meat Science*, 2003). Juiciness is more difficult to evaluate but it can be influenced by the structure of meat and its water binding capacity (for review see Hocquette J F et al., *Ital J Anim Sci*, 2005). However, Renand et al., *Meat Science*, 2001, have shown that only less than one third to a quarter only of the variability in tenderness and flavor can be explained by the variability in muscle characteristics of live animals.

Muscle biological characteristics are under the control of several genes expression. Functional genomics (which includes analysis of the transcriptome and proteome) provides news opportunities for determining the molecular processes related to meat quality (Eggen A. et al., *Meat Science*, 2003). Microarray technology enables multiple genes associated with variation in different sensory traits to be identified. However until now, only few studies have been conducted in this connection either in pigs (Plastow G S et al., *Meat Science*, 2005), or in cattle (Sudre K et al., *Meat Science*, 2005; Wang Y H et al., *Mamm Genome*, 2005.), mainly due to the lack of appropriate and specific tools in livestock species. Therefore, a great deal of effort has been devoted to the preparation of cDNA arrays specific for bovines (for instance, see Bernard C et al., *J Physiol Pharmacol*, 2005 and Lehnert S A et al., *Australian Journal of Experimental Agriculture*, 2004). In parallel, new technologies based on oligonucleotide arrays have been developed as well as an accurate selection of muscle-specific probes from studies in mammals (Lamirault G et al., *J Mol Cell Cardiol*, 2006).

Various methods of meat tenderness detection are known in order to assess whether a meat is tender. In particular, studies have been made of the physico-chemical properties of the muscle have been made. Indeed, the principle of comparing the biochemical characteristics and the sensory characteristics of the meat is known. Within the framework of this comparison, it has been shown that biochemical characteristics explain individually more than 25% of the variability in tenderness (Renand et al., *Meat Science* 2001; Brouard et al., *Rencontres Recherches Ruminants* 2001; review by Hocquette et al., *Italian Journal of Animal Science* 2005).

Other studies have demonstrated the involvement of genes in the tenderness of meat. More particularly, it has been shown that these genes have effect on the molecular composition of the muscle fibers. In particular, genomic markers associated with the tenderness of the meat are known. In the document US 2005/0181373A1, a gene encoding for a neutral protease activated by calcium or mu-calpain is described, which is used to initiate an identification process of different populations or breeds of ruminant mammals such as bovines.

In the document WO02/064820A1, a gene encoding for calpastatin (CAST) is described, which is used to identify animals which provide tender meat.

DISCLOSURE OF THE INVENTION

The inventors have discovered, surprisingly, a DNAJA1 bovine gene (or the nucleotide sequence SEQ ID No 1) which is associated with the phenotype relating to the tenderness of a given meat, and the expression product of which is a protein which does not form part of the molecular composition of the muscle fiber. Equally surprisingly, this expression product also allows the identification of a tender meat all the more in that it is more weakly expressed with regard to another expression product deriving from meat which is not particularly tender. By meat being not particularly tender, it is understood that it is a meat that it is known to be no tender with regard to another meat issued from an other place of the same animal or to the same meat type issued from another animal. A meat that it is not particularly tender is assessed also in function of sensorial analyses criteria that are explaining hereafter (see materials and methods, results).

A meat is a muscle or a part of a muscle of an animal that is eaten after cooking this muscle.

This gene is differentially expressed between muscles which produce tender beef and muscles which produce tough beef whereas another gene (e.g. cyclophilin B gene) is not differentially expressed between the same types of muscles.

This bovine DNAJA1 gene was discovered via an oligonucleotide stemming from the murine DNAJA1 gene. SEQ ID No 1 sequence corresponding to the bovine gene comprises 88% of sequence similarity with the corresponding murine nucleotide sequence. The bovine sequence encodes for a protein which is a member of the family of 40 kDa large heat shock proteins. This is a co-chaperone of Hsc70, and appears to play a role in the importing of proteins into the mitochondria The gene corresponding to the DNAJA1 murine sequence allows for the explanation that it is responsible for up to 63% of the variability in meat tenderness.

Accordingly, the object of the invention is the use of a genomic marker associated with the phenotype relating to the meat tenderness from a bovine animal, the said marker comprising a nucleotide sequence corresponding to all or part of the nucleotide sequence SEQ ID No 1, or to all or a part of an allele of the nucleotide sequence SEQ ID No 1, for the implementation of an identification method for sorting ruminant animals of the bovine type with tender meat, and/or for the implementation of an identification method at the moment of slaughter by direct sampling from the carcass of muscle samples which give tender meats.

The invention has an object the use of the marker described above for the implementation of an identification method characterized in that the expression level of SEQ ID No 1 sequence is quantified in a muscle sample and compared to the expression of a control gene.

The invention has also an object the use of the marker above described for the implementation of an identification method characterized in that the expression level of SEQ ID No 1 sequence is quantified in different muscle samples and compared to each other. Thus, a calibration of quality of meat can be carried out according to the tenderness of each meat tested.

This method also allows to select and/or to sort livestock species producing tender meat.

Generally, this invention concerns the differential expression of DNAJA1 gene between different muscle samples which produce either tender or tough beef.

This invention also concerns any already known or any putative new method which aims to quantify the expression level of DNAJA1 gene.

The invention also concerns an oligonucleotide primer comprising from 5 to 50, preferably from 10 to 30 successive nucleotides of the sequence of the marker described above.

The invention also has as an object an antibody directed against a polypeptide resulting from the expression of the marker described above.

The invention also concerns an oligonucleotide primer comprising from 5 to 50, preferably from 10 to 30 successive nucleotides of a control gene. This control gene is in an example the cyclophilin B gene (or SEQ ID No. 6).

The invention as an object an identification method of a tender meat, said meat being taken from a ruminant animal of the bovine type, characterized in that it comprises the steps of:
quantify an expression level of the SEQ ID No 1 sequence in a muscle sample, and
matched this expression level with an other expression level of a control gene.

The invention likewise has as an object an identification method of a tender meat, the said meat being taken from a ruminant animal of the bovine type, characterized in that it comprises the following steps:
purification of the total RNA derived from a muscle sample taken from the animal,
reverse transcription of the RNA to cDNA,
hybridization of two primers described above with a cDNA sequence,
amplification of the DNA sequence between the two hybridized primers,
quantification of the amplified DNA sequence, and
selection of the amount amplified DNA sequence which reveals the tenderness of the meat when a difference exists between the amount of this amplified DNA sequence and a reference amount of the amplified DNA sequence, the said reference amount being derived from a sample of a meat that is not particularly tender.

The invention has as an object a kit for the implementation of the methods just described above, characterized in that it comprises:
at least one pair of oligonucleotide primers such as described above, and
means for amplifying a cDNA sequence.

The kit can comprise in particular the nucleotide sequence SEQ ID No. 2 as the forward primer, and the nucleotide sequence SEQ ID No 3 as the reverse primer. The primer may, however, be of any other sequence contained in a marker such as described above.

The invention likewise relates to an identification method of a tender meat, the said meat being taken from a ruminant animal of the bovine type, characterized in that it comprises the following steps:
purification of the total RNA derived from a sample of meat taken from the animal,
reverse transcription of the RNA into cDNA,
labelling of the cDNA,
hybridization of a sequence of cDNA with the marker described above,
quantification of the labelling intensity of the hybridized cDNA sequence, and
selection of the hybridized cDNA sequence which reveals the tenderness of the meat when a difference exists between the labelling intensity of this hybridized cDNA sequence and a reference labelling intensity of a hybridized cDNA sequence, said reference labelling intensity being derived from a sample of meat that is not particularly tender.

The invention likewise relates to a method of an identification method of a tender meat, the said meat being derived from a ruminant animal of the bovine type, characterized in that it comprises the following steps:
purification of the total proteins deriving from a sample of meat taken from the animal,
incubation of the antibody described above in contact with the total proteins,
detection of the presence of antibody-antigen complexes,
quantification of any of the antibody-antigen complexes,
selection of antibody-antigen complexes when a difference exists between a quantity of antigen-antibody complexes in the sample and a reference quantity of antigen-antibody complexes, the said reference quantity of antigen-antibody complexes being derived from a sample of a meat that is not particularly tender.

The invention relates to a kit for the implementation of the methods just described above, characterized in that it comprises an antibody such as that described above.

In each of the identification methods described above, the sample may in particular be taken on the animal at any age from birth to slaughter of the animal.

BRIEF DESCRIPTION OF THE DRAWINGS

FIG. 4: Nucleotide sequence corresponding to bovine DNAJA1 gene (SEQ ID No 1),

FIG. 5: Nucleotide sequence corresponding to bovine cyclophilin B gene (SEQ ID No 6)

MATERIALS AND METHODS

Animal and Muscle Samples

Figure 1:
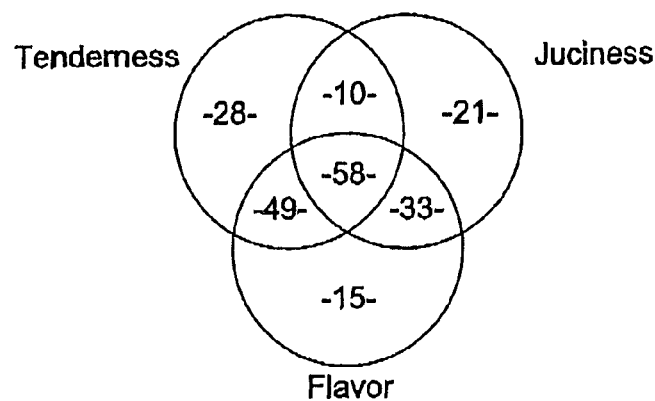
FIG. 1: Distribution of the 215 differentially expressed genes according to tenderness, juiciness and flavor.

This study was conducted with 25 young Charolais bull calves from an INRA experimental herd, weaned at 32 weeks and then kept in an open shed. They were fed a complete pelleted diet distributed ad libitum with a limited amount of straw until slaughter. Thirteen animals were slaughtered at 15 months of age and 12 at 19 months of age. The warm carcass and the internal fat deposit weights were recorded. The next day the 6$^{th}$ rib was dissected and the carcass composition (muscle and fat contents) was estimated using the Robelin & Geay prediction equation (Robelin J et al. *Annales de Zootechnie*, 1975).

Bull calves were progeny of 12 Charolais sires divergently selected on their muscle growth capacity among 80 progeny-tested sires. This progeny testing was previously conducted in this herd with 793 slaughtered bull calves. The sires were ranked on a synthetic index combining their breeding value for a high muscle weight and a low carcass fat percentage. The sires used for creating the current generation of experimental animals were chosen from extremes of the distribution of this selection index. The breeding value of the 25 experimental animals was estimated in an animal model using all information available. They were ranked on a similar synthetic index as their sires. *Longissimus thoracis* muscle (red and oxidative muscle, LT) was excised from each animal within less than ten minutes after slaughter.

The samples were immediately frozen in liquid nitrogen and stored at −80° C. until analyzed.

Biochemical and Mechanical Studies

Glycolytic and oxidative metabolisms were studied by measuring respectively lactate dehydrogenase (LDH, EC 1.1.1.27) activity (Ansay M., *Annales de Biologie Animale Biochimie Biophysique*, 1974) and isocitrate dehydrogenase (ICDH, EC 1.1.1.42), citrate synthase (CS, EC 2.3.3.1) and cytochrome-c oxidase (COX, EC 1.9.3.1) activities (Briand M, et al. *Eur J Appl Physiol Occup Physiol*, 1981). Enzyme activities were expressed in μmol per min and per g of muscle.

Total collagen content was measured as described by Listrat et al., *Meat Science*, 1999. The data (means of triplicates) were expressed in μg of hydroxyproline per mg dry matter (Listrat A et al., *Meat Science*, 2004).

The histological architecture was revealed by azorubin staining on serial cross-sections of 10 μm thickness, prepared using a cryotome at −20° C. The stained sections were analyzed under a microscope and two randomly selected images were captured. Mean fiber area was determined using an image analysis system (Visilog, NOESIS, France).

Total lipids were extracted three times for 1 min in chloroform-methanol (2:1, v/v) at room temperature according to the method of Folch et al. *J Biol Chem*, 1957 and determined gravimetrically. Triglycerides were determined from total lipid extracts as described by Leplaix-Charlat et al. *J Dairy Sci*, 1996. Phospholipids were analyzed from total lipids extracts by colorimetry after mineralization of organic phosphorus according to the method of Bartlett, *J Biol Chem*, 1959.

Meat texture was evaluated by the measurement of Shear Force with a Warner-Brätzler device.

Sensory Assessment

LT steaks were vacuum packaged, aged at 2-4° C. for 14 days post-mortem, and frozen. Steaks were thawed rapidly under flowing water. The following day, the steaks were grilled to a core temperature of 55° C. and immediately served to panelists. A total of 10-12 trained panelists was used in each test session. They evaluated eight meat samples, presented sequentially in each session. They scored initial tenderness and overall tenderness, juiciness and flavor intensity on 10-point scales: from 1 (tough; dry; less tasty) to 10 (tender; juicy; tasty). Meat samples from different bull calves of the same slaughter age group were randomly presented to the panelists. Each sample was tested twice by each panelist in two different sessions. Scores were averaged over the different panelists for each animal.

Animal Classification According to Meat Sensory Quality

Each animal was classified according to the score attributed to its meat for each sensory trait (tenderness (T), juiciness (J) and flavor (F)). For each criterion, eight animals (4 per age group) were chosen among extremes of the distribution to perform comparisons between high (+) and low (−) meat quality scores of tenderness, flavor and juiciness. Table 1 shows animals which were selected in different traits.

TABLE 1

Classification of animals of 15- (white) and 19- (gray) month-old according to the scores attributed to their meat for each sensory quality (T, Tenderness; J, Juiciness; F, Flavor)

| Animals | Tenderness | Juiciness | Flavor |
|---|---|---|---|
| 2531 | T− | | |
| 2533 | | J+ | |
| 2544 | T+ | J+ | F+ |
| 2547 | | | F+ |
| 2548 | T+ | J+ | F+ |
| 2556 | T+ | J− | |
| 2560 | | J− | |
| 2567 | | J− | F− |
| 2578 | | J+ | |
| 2582 | T− | | F− |
| 2585 | T− | J− | F− |
| 2587 | | | F+ |
| 2588 | T+ | | |
| 2594 | T− | | F− |

+ and −: high and low meat quality scores respectively.

Microarray Experiments

Transcriptomic analysis was performed using microarrays, prepared at the West Genopole transcriptome platform, and on which 50-mer oligonucleotides probes (MWG Biotech) were spotted. The oligonucleotides were designed from 3861 human and 1557 murine genes which are implicated in normal and pathological skeletal and cardiac muscle. The 5418 genes that were represented on the microarray were spotted in triplicate with 2898 control spots (buffer and empty). These genes encode proteins of which biological process were classified in Gene Ontology (http://cardioserve.nantes.inserm.fr/ptf-puce/myochips_fr.php).

Particularly, one of the oligonucleotide probes which is spotted is an oligonucleotide sequence coming from the murine DNAJA1 gene.

Total RNA was extracted from Longissimus thoracis muscle, using TRIZOL® Reagent (Life Technologies). RNA quality was assessed using an Agilent 2100 bioanalyser (Agilent Technologies, Palo Alto, USA). In microarray experiments, each sample was compared with a reference pool composed of Longissimus thoracis muscle transcripts isolated from 19-month-old animals. Reverse-transcription and indirect labelling were performed from 4×15 µg of total RNA from each sample using the CyScribe cDNA Post Labelling Kit (Amersham Pharmacia Biotech) as described in the manufacturer's protocol. Samples from each animal were labeled individually with Cy3 and mixed with an equal amount of the reference pool labeled with Cy5. Then, slides were pre-incubated with 40 µl of a hybridization solution containing Denhardt 5×, yeast tRNA (0.5 µg/µl), polyA RNA (0.5 µg/µl), SSC 3.5×, SDS 0.3% and formamide, and hybridized to the microarrays. The incubation was performed at 42° C. for 17 hrs. Four independent hybridizations were performed for each animal.

After washing, hybridized arrays were scanned by fluorescence confocal microscopy (Affymetrix 428™ Array Scanner). Measurements were obtained separately for each fluorochrome at 10 µm/pixel resolution.

Data Analyses and Statistics

Hybridization signal quantification was performed with the Genepix Pro 6.0 image analysis software (Axon Instruments, Inc, Union City, USA). Expression values were normalized using MADSCAN (http://cardioserve.nantes.inserm.fr/mad/madscan/ and Le Meur N. et al., Nucleic Acids Res, 2004) which combines the rank invariant and lowess fitness methods with spatial normalization. Outliers which were detected within arrays (based on triplicate spot replicates) and between arrays (based on the replicates hybridizations×triplicate spots) were eliminated from further analysis. Then, MADSCAN attributed a score according to spot quality. The main criteria were the background level, the signal to noise ratio, the diameter and the saturation level. Genes which had more of 50% of lacking expression values were also excluded of analyses. The identification of differentially expressed genes was performed using Significance Analysis of Microarrays (SAM) (Tusher V G et al., Proc Natl Acad Sci USA, 2001). Ontology of differential expressed genes, notably biological process and metabolic pathway were determined using PANTHER classification system (Thomas P D, et al., Nucleic Acids Res, 2003). A hierarchical clustering (Average linkage and Pearson correlation) was performed using Genesis software (Sturn A, et al., Bioinformatics, 2002) in order to identify similar expression profiles between differentially expressed genes. These genes were used for a subsequent analysis using BiblioSphere Pathway Edition tool from the Genomatix. Suite (http://www.genomatix.de/), a data-mining solution for extracting and analyzing gene relationships from literature databases and genome-wide promoter analysis.

The study was performed according to the standards MIAME (Minimum Information About a Microarray Experiment (Brazma A, et al., Nat Genet, 2001). The data discussed in this publication have been deposited in NCBIs Gene Expression Omnibus (GEO, http://www.ncbi.nlm.nih.gov/geo/) and are accessible through GEO Series accession number GSE5561.

In order to calculate percentage of meat sensory trait variability explained by muscle characteristics or gene expression levels or both, a correlation study and a principal component analysis were performed using the Statistica software (StatSoft, France).

Real-Time RT-PCR

A selection of differential expressed genes was validated by real time RT-PCR (Reverse Transcription—Polymerase Chain Reaction). mRNA levels were assessed using the LightCycler® FastStart DNA Master SYBR Green I kit (Roche Diagnostics Gmbh, Mannheim, Germany) and selected gene-specific primer pairs, table 2, according to the manufacturer's instructions.

TABLE 2

Primer sequences used in quantitative real-time PCR

| Gene Symbol | Forward primer (5") | Reverse primer (3") |
|---|---|---|
| CPT1B | CTTCCACGTCTCCAGCAAGTTTCCGGAGATGTTCTTGGAG (SEQ ID No 9) | (SEQ ID No 20) |
| X1kd1 | GCCGATGATAGCAACCCTAA (SEQ ID No 10) | GCTTGCTTGGTTCTCTGGTC (SEQ ID No 21) |
| NDUFB4 | CAAGATGTCGTTCCCCAAGT (SEQ ID No 11) | CCAAGGCAGGATCTTCGATA (SEQ ID No 22) |
| JMJD1B | GTTGCATCAAAGTCGCAGAA (SEQ ID No 12) | GCTTCACAGGGGAGTTTGAA (SEQ ID No 23) |
| MYH7 | CACCAACCTGTCCAAGTTCC (SEQ ID No 13) | ACTGGGAGCTTCAGTTGCAC (SEQ ID No 24) |
| TPM3 | CTGGAGGAGGAGCTGAAGAA (SEQ ID No 14) | CAGCTTGGCTACCGATCTCT (SEQ ID No 25) |
| PLN | ACTTGGCTGGCAGCTTTTTA (SEQ ID No 15) | ACTGGGATTGCAGCAGAACT (SEQ ID No 26) |
| ATP2A2 | TCTGCCTGTCGATGTCACTC (SEQ ID No 16) | GTTGCGGGCCACAAACTT (SEQ ID No 27) |
| DNAJA1 | AGGGTCGCCTAATCATTGAA (SEQ ID No 2) | TCCTCGTATGCTTCTCCATTG (SEQ ID No 28) |
| CSRP3 | ATGCGGAAAGTCGGTCTATG (SEQ ID No 17) | ACCTGTAGGGCCGAAGTTTT (SEQ ID No 29) |
| CRYAB | CGCCATTACTTCATCCCTGT (SEQ ID No 18) | TCACTGGTGGGAACTTTTC (SEQ ID No 30) |
| HSPB1 | CGTTGCTTCACTCGCAAATA (SEQ ID No 19) | TACTTGTTTCCGGCTGTTCG (SEQ ID No 31) |

All primer sequences were designed using Primer3 software. The primer annealing temperature is 60° C.

A control cDNA dilution series was created for each gene to establish a standard curve to which results expressed in pg/µmol referred. Each reaction was subjected to melting curve analysis to confirm single amplified products.

Comparison Between Expression Levels of a Sample Gene and a Control Gene

From a muscle sample, a first amount of DNAJA1 gene or SEQ ID No 1 sequence expression level is firstly measured after PCR amplification and after micro array experiments. From this same muscle sample, a second amount of cyclophilin B gene expression level is also measured after PCR technique and after micro array experiments, table 8.

The primers used for amplified a part of the cyclophilin B sequence (NM_174152, 854 pb, Bos taurus peptidylpropyl isomerase B) are showed in example in FIG. 5 from the SEQ ID No 6 sequence. A forward primer sequence (or SEQ ID No 7 sequence) is chosen from the nucleotide 170 to the nucleotide 189 of the SEQ ID No 6 sequence. A reverse primer (or SEQ ID No 8 sequence) is chosen from the nucleotide 320 to the nucleotide 339 of the SEQ ID No 6 sequence. The nucleotide sequence that will be amplified will be the nucleotide sequence starting from the nucleotide 190 to the nucleotide 319 of the SEQ ID No 6 sequence.

TABLE 3

Expression levels of DNAJA 1 gene and cyclophilin B
(CYCLOB) gene by RT-PCR (PCR) or following microarray experiments
(array) in muscle samples from 15-month-old or 19-month-old young bulls
which give either tender (T+) or tough (T−) beef.

| Age (months) | N° animal | Tenderness score | T+ vs T− | DNAJA1 (PCR) | DNAJA1 (array) | CYCLOB (PCR) | CYCLOB (array) |
|---|---|---|---|---|---|---|---|
| 15 | 2548 | 6.96 | T+ | 1.33E−03 | −0.45 | 2.66E−04 | 0.14 |
| 15 | 2556 | 7.1 | T+ | 2.18E−03 | −0.04 | 1.96E−04 | 0.23 |
| 19 | 2544 | 6.12 | T+ | 1.51E−03 | −0.06 | 1.88E−04 | 0.19 |
| 19 | 2588 | 5.62 | T+ | 1.68E−03 | 0.17 | 2.52E−04 | −0.01 |
| 15 | 2585 | 3.11 | T− | 2.62E−03 | 0.45 | 2.06E−04 | 0.15 |
| 15 | 2582 | 3.26 | T− | 4.57E−03 | 0.48 | 2.96E−04 | 0.08 |
| 19 | 2594 | 3.73 | T− | 3.42E−03 | 0.76 | 3.00E−04 | 0.2 |
| 19 | 2531 | 3.49 | T− | 2.31E−03 | 0.21 | 2.12E−04 | 0.28 |

Results

Meat Sensory Traits and Muscle Characteristics

A correlation study was performed in order to explain meat sensory variability by muscle characteristics. The correlation coefficients between the 11 measured muscle traits and the sensory scores are reported in Table 3.

TABLE 4

Correlation coefficients of muscle characteristics[1] with sensory scores (tenderness, juiciness and flavor)

| | COX | CS | ICDH | LDH | Lipids | Phospho Lipids | Triglycerides | WB | Water loss | Collagen | Fiber area |
|---|---|---|---|---|---|---|---|---|---|---|---|
| Tenderness | 0.37 | 0.05 | 0.50 | −0.20 | 0.15 | 0.15 | 0.23 | −0.36 | 0.30 | 0.15 | −0.03 |
| Juiciness | 0.30 | −0.03 | −0.15 | 0.14 | −0.50 | −0.03 | −0.45 | 0.02 | 0.03 | 0.28 | −0.04 |
| Flavor | 0.58* | −0.09 | −0.16 | 0.01 | −0.31 | −0.35 | −0.26 | −0.05 | 0.31 | 0.44 | −0.07 |

*|r| ≥ 0.53: $P < 0.05$, level of significance

[1]Cytochrome-c oxidase activity (COX); citrate synthase activity (CS); isocitrate dehydrogenase activity (ICDH); lactate dehydrogenase activity (LDH); lipid content (Lipids); phospholipid content (Phospholipids); triglyceride content (Triglycerides), Warner-Brätzler shear force (WB); cooking water loss (Water loss); total collagen content (Collagen); muscle fiber area (Fiber area).

Tenderness variability was predominantly related to ICDH and COX activities (oxidative metabolism) and to Warner-Brätzler shear force. Juiciness one's tended to be explained by total lipid and triglyceride contents and COX activity. The latter as well as collagen content appeared to be correlated with flavor. Each muscle characteristic, alone, explained less than 33% of flavor variability and less than 25% of tenderness and juiciness variability. Together, these characteristics accounted for up to 50% of sensory trait variability.

Gene Expression Changes Associated with Meat Sensory Quality

Data Analysis

The hybridization results showed that, among the 5418 genes represented on the chip, an average of 4497 (83%) gave valid expression values. Moreover, a low technical variability was observed between four different arrays for each sample (CVmean=11.3%) from valid hybridization signals showing a good reproducibility of the experimentation.

Two groups of SAM analyses (FDR≦1%) were performed to determine gene expression changes associated with tenderness, juiciness or flavor scores. These analyses were made for each sensory trait: one per age group (15- and 19-month old respectively) and another analysis of all the data (i.e. 15- and 19-month old together). Combination of the results is presented in Table 4.

TABLE 5

Number of significantly differentially expressed genes according to meat sensory quality

| | Tenderness (T+ vs T−) | Juiciness (J+ vs J−) | Flavor (F+ vs F−) |
|---|---|---|---|
| Differentially expressed genes | 615 | 1005 | 799 |
| Total | 1772 | | |
| Differentially expressed genes with Fold Change > 1.4 in at least one condition | 146 | 122 | 155 |
| Total | 215 | | |

Differential expression was based on SAM analysis (FDR≦1%). The total number of genes does not correspond to the sum of the numbers above, because some genes are common to several analyses. T+ vs T−, J+ vs J− and F+ vs F− analyses compared respectively the most and the least tender meats, the juiciest and the least juicy meats and the tastiest and the least tasty meats.

Analyses according to tenderness scores (T+ vs T−) identified 615 differentially expressed genes. The analyses according to meat juiciness (J+ vs J−) allowed identifying 1005 genes whose expression varied between the 2 conditions. Lastly, 799 genes had their expression significantly altered between the tastiest and the least tasty meats (F+ vs F−). Gathering all differentially expressed genes, table 4, only 1772 were associated with tenderness and/or juiciness and/or flavor, some of them being common to at least 2 sensory traits. Two hundred fifteen of the 1772 genes were up-regulated (Fold change>1.4) or down-regulated (Fold change<0.71) in at least one condition.

Homology and Gene Ontology Analysis

The 215 most interesting genes were represented by 159 human and 56 murine oligonucleotides. However, these genes taken as a whole are not yet all identified in the bovine genome. While some of them are known (37%), others correspond to EST sequences (52%). One hundred eighty five of the oligonucleotide had a sequence homology with the bovine genome and among them, 84% had a high similarity (>80%).

These differentially expressed genes were mostly involved in signal transduction, different metabolic pathways and their regulation including protein and nucleic acid metabolism, cell structure and motility, developmental processes, muscle contraction, immunity and defense and transport. However the ontology of one fifth of these genes was still unknown and no main pathway could be associated with these genes.

Differentially Expressed Genes According to Three Sensory Traits

Taken into account all the different analyses, 58 genes among the 215 were differentially expressed according to tenderness, juiciness and flavor all together. Some genes were common only to two sensory traits: 10 to tenderness and juiciness, 33 to flavor and juiciness and 49 to tenderness and flavor. Finally, 29, 21 and 15 genes were differentially expressed with FC>1.4 and specific of tenderness, juiciness and flavor respectively, FIG. 1.

Differentially expressed genes according to the 3 criteria (n=58) were distributed as follows: 33 showed an over-expression in muscles whose meats were the most tender, juiciest and tastiest. Nine were down-regulated in the same samples and 16 had different expression profiles between tenderness, juiciness and flavor, table 5.

TABLE 6

Up an down-regulated genes according to tenderness, juiciness and flavor.

| | Symbol | Gene name | Tenderness | Juiciness | Flavor | Hierarchical clustering |
|---|---|---|---|---|---|---|
| Up-regulated genes 15- and 19-month-old | CPT1B | carnitine palmitoyltransferase 1B (muscle) | ** | ** | ** | Cluster 1 |
| | Xlkd1 | extra cellular link domain-containing 1 | ** | ** | ** | Cluster 1 |
| | NDUFB4 | NADH dehydrogenase (ubiquinone) 1 beta subcomplex, 4, 15 kDa | ** | ** | ** | Cluster 1 |
| | JMJD1B | jumonji domain containing 1B | ** | ** | ** | Cluster 1 |
| | LAMA3 | laminin, alpha 3 | ** | ** | ** | Cluster 1 |
| | FLJ12193 | hypothetical protein FLJ12193 | ** | ** | ** | Cluster 1 |
| | Npm3 | nucleophosmin/nucleoplasmin, 3 | ** | ** | ** | Cluster 1 |
| | Cyp2c50 | cytochrome P450, family 2, subfamily c, polypeptide 50 | ** | ** | ** | Cluster 1 |
| | TRIM55 | tripartite motif-containing 55 | ** | ** | ** | Cluster 1 |
| | Cbr2 | carbonyl reductase 2 | ** | ** | ** | Cluster 1 |
| | C:6970 | Homo sapiens chromosome 5 clone CTD-2151N11 | * | ** | ** | Cluster 1 |
| | PRRX2 | paired related homeobox 2 | * | ** | ** | Cluster 1 |
| | OTOR | Otoraplin | * | ** | ** | Cluster 1 |
| | CACNA1C | calcium channel, voltage-dependent, L type, alpha 1C subunit | * | ** | ** | Cluster 1 |
| | Ireb2 | iron-responsive element binding protein 2 | * | ** | ** | Cluster 1 |
| 15-month-old | PRKAG1 | protein kinase, AMP-activated, gamma 1 non-catalytic subunit | * | ** | ** | Cluster 1 |
| | NID1 | nidogen 1 | * | ** | * | Cluster 1 |
| | MPDZ | multiple PDZ domain protein | * | ** | * | Cluster 1 |

TABLE 6-continued

Up an down-regulated genes according to tenderness, juiciness and flavor.

|  | Symbol | Gene name | Tenderness | Juiciness | Flavor | Hierarchical clustering |
|---|---|---|---|---|---|---|
|  | CGREF1 | cell growth regulator with EF-hand domain 1 | * | * | ** | Cluster 1 |
|  | LGALS3BP | lectin, galactoside-binding, soluble, 3 binding protein | * | * | ** |  |
|  | PHF13 | PHD finger protein 13 | ** | * | ** |  |
|  | SLC25A12 | solute carrier family 25 (mitochondrial carrier, Aralar), member 12 | * | ** | * |  |
|  | CCNA1 | cyclin A1 | * | ** | * |  |
|  | RTN1 | reticulon 1 | ** | ** | ** | Cluster 2 |
|  | MYH7 | myosin, heavy polypeptide 7, cardiac muscle, beta | ** | ** | ** | Cluster 2 |
|  | Tpm3 | tropomyosin 3 | ** | ** | ** |  |
|  | PLN | Phospholamban | ** | ** | ** | Cluster 2 |
|  | C:3400 | Homo sapiens genomic DNA, chromosome 11 clone: RP11-867G2 | ** | ** | ** | Cluster 2 |
|  | CCR5 | chemokine (C-C motif) receptor 5 | ** | * | ** | Cluster 2 |
|  | STK1 | stem cell tyrosine kinase 1 (STK-1) gene, exons 9, 10, and 11 and partial cds | * | * | ** | Cluster 2 |
|  | ANXA10 | annexin A10 | * | ** | * | Cluster 2 |
| Down-regulated genes | ATP2A2 | ATPase, Ca++ transporting, cardiac muscle, slow twitch 2 | * | ** | * | Cluster 2 |
|  | CASP3 | caspase 3, apoptosis-related cysteine peptidase | * | * | ** | Cluster 2 |
|  | PDK4 | pyruvate dehydrogenase kinase, isozyme 4 | ** | ** | ** |  |
|  | DNAJA1 | DnaJ (Hsp40) homolog, subfamily A, member 1 | ** | ** | ** |  |
|  | CSRP3 | cysteine and glycine-rich protein 3 (cardiac LIM protein) | ** | ** | ** |  |
|  | CRYAB | crystallin, alpha B | ** | ** | ** |  |
|  | THOC3 | THO complex 3 | ** | ** | ** |  |
|  | FLNC | filamin C, gamma (actin binding protein 280) | * | ** | ** |  |
|  | RGS2 | regulator of G-protein signalling 2, 24 kDa | * | ** | ** |  |
|  | HSPB1 | heat shock 27 kDa protein 1 | ** | * | * |  |
|  | Pbef1 | pre-B-cell colony enhancing factor 1 | * | ** | * |  |

* Fold Change <1.4;
** Fold Change >1.4

Ten of the 33 genes appeared to be specific to the 15-month-old animals whereas the remaining 23 were differentially expressed at both 15 and 19 months of age. A hierarchical classification of the 215 differentially expressed genes showed that 9 of the 15 months specific genes and 19 of the 23 others genes were grouped in two clusters.

Conversely, the 9 down-regulated genes were classified into different clusters. However, 5 of these genes had a high differential expression (FC>1.4) for the 3 criteria (tenderness, juiciness and flavor). Real time RT-PCR experiments realized on twelve genes selected among up- and down-regulated genes, confirmed differential expressions according to tenderness, juiciness and flavor for all genes, except two (CPT1B and NDUFB4) for which only 15-months specific differential expressions were validated, table 6.

TABLE 7

Validation by real time RT-PCR of 12 gene differential expressions

|  |  | Tenderness | | Juiciness | | Flavor | |
| --- | --- | --- | --- | --- | --- | --- | --- |
|  |  | 15 | 19 | 15 | 19 | 15 | 19 |
| Up-regulated genes | CPT1B | 1.7 *1* | 1.5 *0.8* | 1.5 *2* | 1.9 *0.7* | 1.6 *1.5* | 1.6 *0.8* |
|  | Xlkd1 | 1.7 *1.5* |  | 1.5 *2.4* | 1.7 *1.2* | 1.6 *1.1* | 1.5 *1.2* |
|  | NDUFB4 | 1.7 *1.6* |  | 1.7 *1.3* | 1.8 *0.6* | 1.6 *1.5* | 1.7 *0.8* |
|  | JMJD1B | 1.4 *1.2* |  | 1.4 *1.6* | 1.7 *1.7* | 1.6 *1.4* | 1.8 *1.3* |
|  | MYH7 | 1.7 *2.8* |  | 1.5 *1.3* |  | 2 *2.7* |  |
|  | TPM3 | 1.8 *2.4* |  | 1.5 *1.6* |  | 1.9 *2.9* |  |
|  | PLN | 2.1 *3.5* |  | 1.6 *2.3* |  | 2.1 *3.8* |  |
|  | ATP2A2 | 1.3 *1.2* |  | 1.4 *1.6* | 1.3 *1.4* | 1.4 *1.3* |  |
| Down-regulated genes | DNAJA1 | 1.6 *1.6* | 1.4 *2* | 1.4 *1.1* |  | 1.5 *1.4* |  |
|  | CSRP3 |  | 1.6 *2.2* |  | 6.4 *7.2* |  | *4* |
|  | CRYAB | 1.7 *1.7* |  |  | 2.2 *4.7* |  | 1.8 *4.4* |
|  | HSPB1 | 2.2 *1.8* |  |  | 1.3 *2.9* |  | 1.4 *2.8* |

The fold change value according to microarray experiment and real time RT-PCR (italics) is indicated for each gene.

Meat Sensory Traits and Microarray Data

The correlation matrix between the sensory scores and the differentially expressed genes was determined in order to show percentage of meat sensory traits variability explained by the expression level of these genes. A specific attention was brought to up-regulated genes belonging to cluster 1 and to the 5 down-regulated genes with a high fold change. The correlation coefficients are reported in table 7.

TABLE 8

Correlation coefficients of up- and down-regulated genes with sensory scores (tenderness, juiciness and flavor)

|  |  | Tenderness | Juiciness | Flavor |
| --- | --- | --- | --- | --- |
| Up-regulated genes | CPT1B | 0.48 | 0.61 * | 0.65 * |
|  | Xlkd1 | 0.50 | 0.64 * | 0.65 * |
|  | NDUFB4 | 0.40 | 0.62 * | 0.65 * |
|  | JMJD1B | 0.44 | 0.67 ** | 0.77 ** |
|  | LAMA3 | 0.48 | 0.59 * | 0.67 ** |
|  | FLJ12193 | 0.58 * | 0.66 ** | 0.74 ** |
|  | Npm3 | 0.59 * | 0.59 * | 0.65 * |
|  | Cyp2c50 | −0.31 | 0.05 | 0.01 |
|  | TRIM55 | 0.54 * | 0.68 ** | 0.76 ** |
|  | Cbr2 | 0.65 * | 0.64 * | 0.70 ** |
|  | C:6970 | 0.45 | 0.68 ** | 0.73 ** |
|  | PRRX2 | 0.36 | 0.59 * | 0.67 ** |
|  | OTOR | 0.49 | 0.70 ** | 0.73 ** |
|  | CACNA1C | 0.41 | 0.67 ** | 0.69 ** |
|  | Ireb2 | 0.49 | 0.60 * | 0.73 ** |
|  | PRKAG1 | 0.43 | 0.62 * | 0.77 ** |
|  | NID1 | 0.31 | 0.50 | 0.59 * |
|  | MPDZ | 0.36 | 0.67 ** | 0.70 ** |
|  | CGREF1 | 0.44 | 0.65 * | 0.72 ** |
| Down-regulated genes | PDK4 | −0.27 | −0.17 | −0.40 |
|  | DNAJA1 | −0.80 ** | −0.40 | −0.52 |
|  | CSRP3 | −0.14 | −0.54 * | −0.65 * |
|  | CRYAB | −0.30 | −0.37 | −0.47 |
|  | THOC3 | −0.16 | −0.38 | −0.31 |

\* |r| ≧ 0.53: p < 0.05;
\*\* |r| ≧ 0.66: p < 0.01

Eighteen of 19 up-regulated genes were highly correlated with both meat juiciness and flavor and they explained up to 50% and 60% of juiciness and flavor variability respectively. Four of them were also related to tenderness (FLJ12193, Npm3, TRIM55 and Cbr2) and accounted for 30 to 42% of its variability. One down-regulated gene (DNAJA1) had a strong negative correlation with tenderness and explained 63% of its variability (see also FIG. 3).

Meat Sensory Traits, Muscle Characteristics and Differentially Expressed Genes

Figure 2:
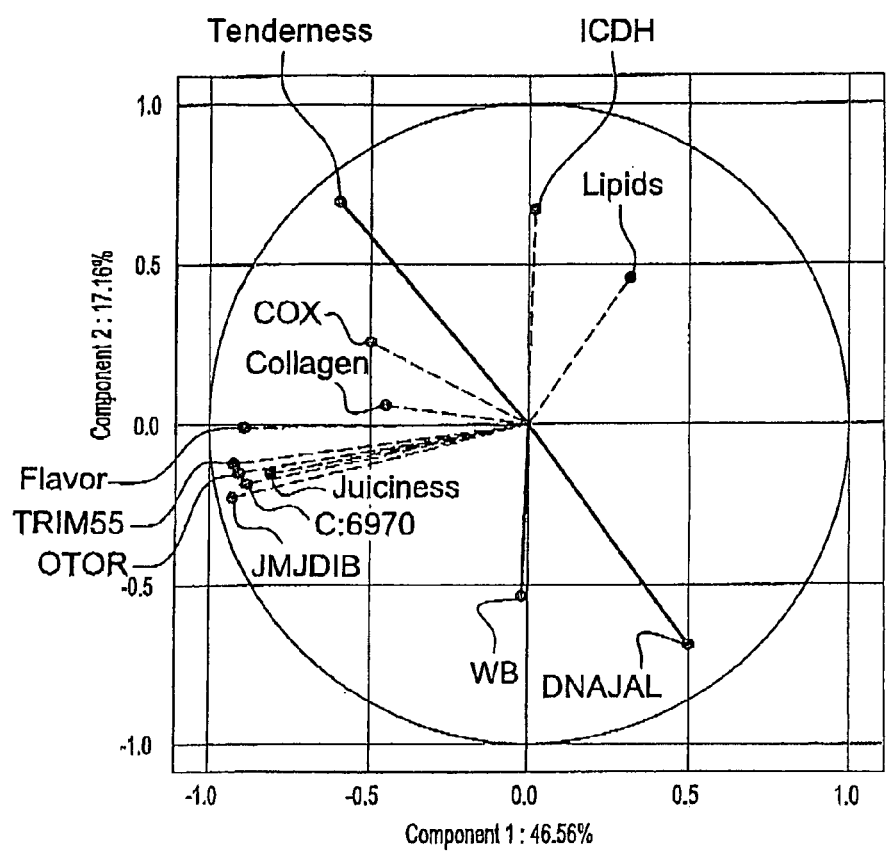
FIG. 2: Principal component analysis of muscle characteristics and differentially expressed genes related to sensory traits (tenderness, juiciness and flavor)

In order to calculate the percentage of variability of sensory quality explained by both muscle biochemical characteristics and gene expression levels, a principal component analysis was performed. For this, muscle characteristics and differentially expressed genes which were the most related to tenderness, juiciness and flavor were kept for the analysis according to Tables 3 and 7. Up to 65% of sensory quality variability were explained by the first two components, FIGS. 2 and 3.

Muscle characteristics are the cytochrome-c oxidase activity (COX), the isocitrate dehydrogenase activity (ICDH), the lipid content (Lipids), the Warner-Brätzler shear force (WB) and total collagen content (Collagen).

This analysis showed also a higher correlation between sensory traits and gene expression levels than between sensory traits and muscle biochemical characteristics.

Regulatory Networks

Differentially expressed genes belonging to cluster 1 were used as input data in BiblioSphere Pathway Edition tool in order to identify one or several putative regulatory networks. This approach allowed us to reveal relations between ten genes from cluster 1 and other genes/transcription factors that were co-cited with them according to human databases. Nine of these seem to be regulated by five transcription factors, especially the androgen receptor (AR), the transcription factor Sp1 and the upstream transcription factor 2, c-fos interacting (USF2). These genes contain specific transcription factor binding site into their promoter. AR can regulated NDUFB4, Xlkd1 and CACNA1C genes by binding on the glucocorticoid responsive and related element (V$GREF) into their promoter. PRRX2 and NID1 bind Sp1, a zing-finger protein on the site V$SP1F in their promoter, whereas CPT1B and Ireb2 genes are regulated by another transcription factor USF2, a member of the basic helix-loop-helix leucine zipper family.

Comparison Between Expression Levels of a Sample Gene and a Control Gene

The expression level of the DNAJA1 gene depends on the tenderness of the meat contrary to the expression level of the control gene (or cyclophilin gene) which is not varied, table 8.

DISCUSSION

One major originality of this work is to have identified new biological indicators of beef quality (tenderness, flavor) using transcriptomic approaches. These novel results firstly underline the usefulness of genomics in farm animals. It however refers to the availability and quality of genomic tools and to their utilization in livestock. Secondly, the novel results brought by this study are of prime importance on a physiological point of view for a better understanding of muscle biology related to beef quality.

Transcriptomic Analysis in Farm Animals

Microarray technology is a powerful tool because it allows studying multiple gene expression profiles. Nowadays, analyses of transcriptome are expanding more and more in the major livestock species such as cattle (Hocquette J F et al., *Proceedings of the 2nd International Conference on Cybernetics and Information Technologies, Systems and Applications, Orlando* (Fla., USA), 2005), pigs (Plastow G S. et al., *Meat Science,* 2005) and chicken (Bourneuf E, et al., *Gene,* 2006) but there is still a critical lack of availability of appropriate and specific tools. Therefore, researches were initially conducted to develop cDNA libraries and EST sequence resources from different tissues (Bai Q, et al., *BMC Genomics,* 2003; Hubbard S J. et al. *Genome Res,* 2005, Sudre K. et al. *Mol Cell Probes,* 2005) with the aim of producing cDNA arrays (Bai Q, et al., *BMC Genomics,* 2003; Bernard C. et al., *Journal of Physiological Pharmacology,* 2005, Burnside J. et al. *BMC Genomics,* 2005, Lehnert S A. et al., *Australian Journal of Experimental Agriculture,* 2004). In the same time, the progress in EST availability and in sequencing of various genomes allowed the design and the commercialization of oligonucleotide arrays. However, the latter and especially available bovine arrays are not well adapted to our objectives which are targeted to the muscle tissue in relation with beef quality. So, our choice was turned towards long-oligonucleotide microarrays whose oligonucleotide sequences are specific to skeletal and cardiac muscles. These arrays were however prepared with human or murine muscle sequences. The advantages of oligonucleotide microarrays are to study a higher number of genes and to increase the specificity of hybridization especially as the bovine genome comparative coverage relative to the human genome is about 91% (Everts-van der Wind A. et al., *Proc Natl Acad Sci USA,* 2005). Moreover, in our study, 84% of differential genes of interest had a strong sequence homology with bovine genome (>80%), giving confidence in the results. The results also demonstrated that working in an heterologous system was not a problem due to the high quality and specificity of the arrays since the hybridization percentage (more than 80%) was much higher than in previous studies with human muscle cDNAs (Sudre K. et al., *J Biochem* (Tokyo), 2003) or even compared to bovine cDNAs (Bernard C. et al., *J Physiol Pharmacol,* 2005).

Until now, some gene expression-based researches related to beef quality focused on identification of molecular processes involved in meat quality traits such as toughness and marbling (Lehnert S A. et al., *Australian Journal of Experimental Agriculture,* 2006). Different studies dealt with fetal muscle development (Sudre K. et al., *J Biochem* (Tokyo), 2003), muscle growth potential (Potts J K. Et al., *Anim Genet,* 2003, Sudre K. et al., *Meat Science,* 2005) and with effects of nutritional changes (Byrne K A. et al. *J Anim Sci,* 2005) which all influence the composition of muscle tissue. Other studies were also focused on intramuscular fat development since the latter influences marbling and thus juiciness and flavor (Wang Y H. et al., *Mamm Genome,* 2005; Wang Y H. et al., *Australian Journal of Experimental Agriculture,* 2005). However, none of theses studies clearly aimed the identification of differentially expressed genes according to beef sensory quality especially tenderness, juiciness and flavor.

In order to achieve this goal, the inventors have also taken advantages of the continuous progress in transcriptomic studies. For instance, to assess the real biological variability, the inventors have analyzed the samples of individual animals instead of a pool of representative samples as published before in livestock. To assess the real technological variability, the inventors have performed analyses with four identical arrays per sample in addition to triplicates of oligonucleotides on each slide. The inventors have also exploited the more recent bioinformatics tools and available statistical software such as MADSCAN (Le Meur N. et al., *Nucleic Acids Res,* 2004) and SAM (Tusher V G et al., *Proc Natl Acad Sci USA,* 2001) software. They notably include a rigorous filtering of data, an intensity-dependent normalization step, and a statistical procedure based on data permutations. The results indeed indicated that the biological variability and especially the technical variability were low (22% and 11.3% respectively) making the experiments highly reproducible. This enabled us to minimize both the number of false and negative positives (Le Meur N. et al., *Nucleic Acids Res,* 2004). Most of the differentially expressed genes were indeed validated by real time RT-PCR.

Indicators of Beef Sensory Quality

Longissimus thoracis muscle characteristics studied in this experiment explained individually a quarter to one third maximum of the variability in tenderness, juiciness or flavor as previously shown by Renand et al using a similar experimental design (Renand G. et al., *Meat Science,* 2001). To our knowledge, the muscle characteristics of live animals, including calpain and calpastatin activities, even when all associated together, never explained more than 40% of the variability in tenderness (Veiseth E and Koohmaraie M., *Indicators of milk and beef quality, EAAP Publication* 112, *Wageningen Academic Publishers, Wageningen, The Netherlands,* 2005). This might be explained by our limited knowledge of muscle biology related to beef quality. In order to identify novel muscle characteristics, differences in gene expression profiles were analyzed between high and low meat quality scores of tenderness, flavor and juiciness using microarray technology. Each comparison allowed identifying a great number of differentially expressed genes with a false discovery rate of 0.1% to minimize false positive genes. However, many of them showed a low fold change value, probably due to the low differences between the 2 groups. Therefore, the inventors chose to retain genes which were differentially expressed between the different sensory conditions with a minimal fold change value of 1.4. Thus, only 12% of differential genes (n=215) seemed to be interesting for sensory quality and particularly 42 genes which were differentially expressed according to the three criteria (tenderness, juiciness and flavor). Thirty-three of them appeared to be associated with high sensory quality either in an age-specific manner (e.g. MYH7, PLN, TPM3) or at the two studied ages (e.g. Xlkd1, NDUFB4) and 10 were classified as unfavorable for beef quality (e.g. DNAJA1, CSRP3, CRYAB). However, neither clear biochemical pathway, nor biological process was identified as being highly involved in beef quality. These genes showed indeed different ontologies such as protein and nucleic acid metabolism or signal transduction. Beef sensory quality doesn't seem, therefore, to be related to a specific metabolic pathway nor a biological process (e.g. proteolysis potential at slaughter which would explain the major part of variability in meat tenderness, or lipid and fatty acid metabolism which could play a major role in meat flavor). This supported the hypothesis that beef quality scores each result from a combination of different biological processes (for instance, toughness of connective tissue, meat proteolysis, etc for tenderness) (Maltin C. et al., *Proc Nutr Soc,* 2003).

Specific Indicators of Tenderness

Figure 3:
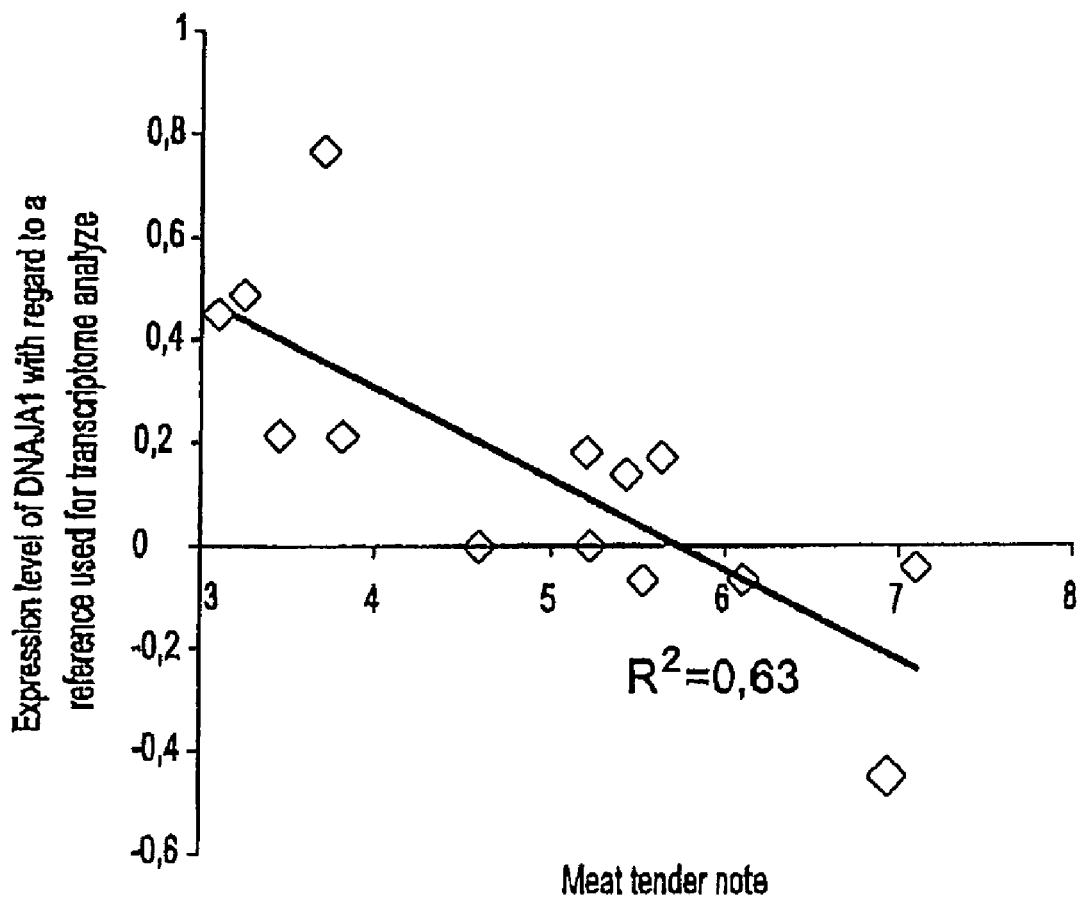
FIG. 3: A diagrammatic representation of the correlation between the tenderness of the meat after 14 days of ageing and the relative level of the expression of the bovine DNAJA1 sequence at the moment of slaughter.

Interestingly, among the five highest down-regulated genes for the three sensory traits, only one was strongly related to tenderness and explained up to 65% of its variability, FIG. 3. This gene called DNAJA1 encodes a member of the large heat shock 40 kDa protein family. This protein is a co-chaperone of Hsc70 and seems to play a role in protein import into mitochondria. Another gene (HSPB1) encoding a heat shock 27 kDa (Hsp27) protein was also under-expressed. Hsp27 belongs to the small heat shock protein (hsp20) family. It is involved in stress resistance and actin organization. Guay et al., *J Cell Sci,* 1997 showed that the over-expression of Hsp27 led to actin polymerization and thus enhanced stability of the actin microfilaments. The inventors can suppose therefore that its under-expression could be in favor of the actin disorganization or degradation. The under-expression observed in T+ muscles could induce a reduced toughness or a higher degradation of actin microfilaments during meat ageing and thus could explain the highest tenderness scores attributed to the meat. The postmortem degradation of actin was indeed shown to contribute the tenderization process of pork (Lametsch R. et al., *J Agric Food Chem,* 2003, Morzel M. et al., *Meat Science,* 2004). Two proteomic studies performed respectively in *Longissimus thoracis* muscle of Blonde d'Aquitaine bull calves and in Semitendinosus muscle of Charolais 15-month-old bull calves with the highest tenderness scores showed also a down-regulation of Hsp27 protein (unpublished proteomic data from our lab). Another gene, CRYAB, encoding αB-crystallin was also under-expressed in the same samples. This protein is also a member of the small heat shock protein family and its stability was shown to be promoted by Hsp27 (Fu L and Liang J J. *Biochem Biophys Res Commun,* 2003). Interestingly, expression of these genes were strongly correlated each other (|r|=0.725, data not shown). AlphaB-crystallin plays an important role in protecting the intermediate filaments since it stabilizes and protects target proteins including desmin by preventing their irreversible aggregation (Goldfarb L G. et al., Brain, 2004, Wang X. et al., *Circ Res,* 2003). The inventors can hypothesize that the under-expression of CRYAB gene could promote degradation of intermediate filaments, and consequently good meat tenderness. The under-expression of αB-crystallin protein was also observed in *Longissimus thoracis* muscle of Blonde d'Aquitaine bull calves with the highest tenderness scores (unpublished proteomic data from our lab).

Specific Indicators of Flavor and Juiciness

Up-regulated genes belonging to the most discriminating cluster (cluster 1), except Cyp2c50, were all strongly correlated to juiciness and flavor scores. Only PRKAG1 gene encoded protein which is involved in fatty acid metabolism. This protein is one of three isoforms of the AMP-activated protein kinase γ sub-unit. It is responsible for the regulation of fatty acid synthesis by phosphorylation of the lipogenic enzyme acetyl-CoA carboxylase and plays an important role in regulating the expression of genes involved in glucose metabolism. Characterization of bovine PRKAG1 gene has just begun (Benkel B. et al., *Mamm Genome,* 2005) and its involvement in beef quality is still unknown. However, others studies in pig have showed that a dominant mutation (denoted RN−) in PRKAG3 gene, encoding another isoform of AMPK γ sub-unit, induced a constitutive activation of AMPK activity, leading to a high glycogen content in skeletal muscle, a low ultimate pH, a reduced water-holding capacity and a reduced yield of cured cooked ham, that has a negative impact on meat quality (Milan D. et al., *Science,* 2000). Hamilton et al., *FEBS Lett,* 2001, reported that a mutation in human PRKAG1 gene, structurally equivalent to RN−, resulted also in an increase in AMPK activity but the possible involvement of PRKAG1 in the regulation of fatness traits remains to be demonstrated.

Regarding the other genes up-regulated in muscles giving the juiciest and tastiest meats, their relation with juiciness and flavor have to be clarified. They were involved in varied biological processes. However, data mining of literature using the Genomatix Bibliosphere Pathway Edition tool indicated that some of these genes were regulated by different transcription factors involved notably in regulation of gene expression especially of adipocyte-specific genes. For example, it has been demonstrated the presence of AR in human preadipocytes and adipocytes suggesting the possible contribution of androgens to the control of adipose tissue development, through regulation by their own receptors (Dieudonne M N. et al., *Am J Physiol,* 1998). Another transcription factor, Sp1 is implicated in the transcriptional regulation of the adipocyte amino acid transporter gene (Zhu Q and Liao K., *Biochem Biophys Res Commun,* 2000). Further analyses have showed that Sp1 mediated glucose activation of the acetyl-CoA carboxylase (ACC) promoter (Daniel S and Kim K H, *J Biol Chem,* 1996). ACC is the rate-limiting enzyme in the biosynthesis of fatty acids. The inventors can suppose that these transcription factors are main regulators but further analyses should be performed to confirm this hypothesis because these genes were not represented on the chip.

The transcription factor USF2 can activate transcription of the hormone-sensitive lipase (HSL) promoter, through E-box motifs in the glucose-responsive region (Smih F. et al. *Diabetes,* 2002). This enzyme catalyses the rate-limiting step in the mobilization of fatty acids from adipose tissue. The oligonucleotide specific of USF2 gene was represented on the Myochip but its expression was not modified according to meat quality. Nevertheless, this can be due to the heterologous system and to a low homology between the oligonucleotide sequence and the corresponding bovine gene.

Although the up-regulated genes were not biologically related to flavor and juiciness, their regulation by some transcription factors give good researching tracks.

From the microarrays experiments realized from tender meats samples and from no tender meats samples, the inventors have identified in particular a common cDNA to each meat sample. This cDNA is hybridized on the oligonucleotide which comes from the DNAJA1 murine gene. The bovine comprises also the DNAJA1 gene. The bovine DNAJA1 cDNA corresponds to the nucleotide sequence SEQ ID No 1, FIG. 4. The inventors are interested to this sequence SEQ ID No 1 since the expression of this sequence is correlated with the meat tenderness. Indeed, according to the experiences realized, the inventors have noted that the expression product of this sequence is highly decreased when this same sequence come from a tender meat, FIG. 3.

Thus, with the aid of the SEQ ID No 1 sequence, the inventors have established at least one genomic marker of the meat tenderness. This marker can comprise all or a part of the SEQ ID No 1 sequence or all or a part of the allele gene derived from the SEQ ID No 1 sequence. In an embodiment of the invention, the SEQ ID No 2 sequence and the SEQ ID No 3 sequence can serve one or the other as a genomic marker. The SEQ ID No 2 sequence comprises 20 oligonucleotides and corresponds to the successive nucleotides sequence extending from the nucleotide 1057 to the nucleotide 1076 of the SEQ ID No 1 sequence, FIG. 4. The SEQ ID No 3 sequence comprises 21 nucleotides and corresponds to the successive nucleotide sequence extending from the nucleotide 1235 to the nucleotide 1255 of the SEQ ID No 1 sequence. These two sequences (SEQ ID No 2 and SEQ ID No 3) can advantageously not only serve as genomic markers of tenderness meat, but also as primers for amplified a nucleotide sequence (or SEQ ID No 5) comprised between these two sequences.

In an other example, the inventors have used a SEQ ID No 4 sequence as marker. This SEQ ID No 4 sequence extending from the 1096 nucleotide to the nucleotide 1145 of the SEQ ID No 1 sequence. The SEQ ID No 4 sequence is a sequence that is hybridized with the oligonucleotide probe coming from the murine DNAJA1 gene and that has been used in the microarray experiences. This SEQ ID No 4 sequence and the murine oligonucleotide have moreover 94% of sequence similarity.

Several identification methods of tender meats can be set up. Each of these identification methods assesses the expression level of DNAJA1 gene. But others identification methods can assess the expression level of other under-expressed gene. Other identification methods can assess also the expression of over-expressed genes like C:3400 gene, PLN gene, Tpm3 gene, Npm3 gene, see tables 5 and 7.

can be based on the quantification of an expression level of the SEQ ID No 1 sequence from a muscle sample to test. Then this expression level is matched with an other expression level of a control gene.

For a preferably embodiments, the DNAJA1 gene is chosen as gene deriving from a muscle sample because it is differentially expressed between muscles which produce tender (T+) and muscles which produce tough (T−) beef samples (table 8). The gene control is for example the cyclophilin gene or SEQ ID No 6 sequence. This gene is chosen because it is not differentially expressed between muscles which produce tender (T+) and muscles which produce tough (T−) beef samples (Table 8).

Others identification methods can be made on the matching of expression level of a gene deriving from a muscle sample with an other expression level of this same gene which derived from a muscle sample which produces meat that is known to be not particularly tender.

A first identification method consists of quantify the expression of the gene based on the SEQ ID No 1 sequence by the general technique of PCR. In a preferred embodiment of the invention, this first identification method is made by the Real Time RT-PCR method (see Bonnet M. et al., J. Nutr., 2000). A total RNA extract of a meat sample is purified. The RNA is transcribed into cDNA. Then, the cDNA is amplified in DNA sequence with primers and means for amplification as DNA polymerase. For example, the primers are the SEQ ID No 2 sequence as forward primer and the SEQ ID No. 3 sequence as reverse primer. Then, the amount of amplified DNA sequence is matched with a reference amount of amplified DNA sequence deriving from the control gene (SEQ ID No 6 gene). The amount of amplified DNA sequence of the meat to test can also be matched with a reference amount of amplified DNA sequence, said reference amount of amplified DNA sequence coming from a meat sample that being not particularly tender. When the amplified DNA sequence amount of the meat sample to test is less important than the reference amplified DNA sequence, it can be considered that the meat deriving from the sample to test is tender.

A second identification method consists to purify RNA of a sample meat. This RNA was transcribed into cDNA. The cDNA is labeled and then hybridized on corresponding oligonucleotide. The oligonucleotide is one of the markers described above. The intensity of labelling of the meat to test is matched with a reference intensity labelling of a cDNA deriving from the control cyclophilin B gene or with a reference intensity of a cDNA deriving from a sample meat that it is not particularly tender. When the intensity of the cDNA of the meat to test is less important than the reference intensity, it can be deduced that the sample meat is tender.

A third identification method consists in the detection of an antigen-antibody complex and the matching between the quantity of this antigen-antibody complex and a reference complex antigen-antibody. The presence of the antigen-antibody complex induces the presence of the DNAJA1 gene. This third identification method permits to deduce that the meat to test is tender when the amount of complex deriving from the meat to test is less important than the reference amount of complex deriving from the control cyclophilin gene or deriving from the meat sample that it is not particularly tender.

Such first, second and third identification methods permit to deduce tenderness degree of a meat collected on a same place from an animal to an other animal. Or, such first, second and third identification methods permit to deduce tenderness degree of a meat to an other meat collected at different place on a same animal.

It can be noted also that these first, second and third identification methods can be also used for other genes for whose the expression is inversely more higher than the expression of this same gene in a reference sample (for example, the gene Npm3, tables 5 and 7).

Validation of DNAJA1 gene expression as a genomic marker for meat tenderness

BACKGROUND AND OBJECTIVES

The DNAJA1 gene alone, encoding a heat shock protein and potentially involved in meat ageing by its anti-apoptotic role, explained 63% of tenderness variability.

Therefore, the aim of this complementary study is to validate DNAJA1 gene expression as a new marker of beef tenderness. To achieve this goal, a real time RT-PCR assessment of DNAJA1 expression was performed on a larger set of samples than previously: DNAJA1 gene expression level was analysed in a total of 49 Longissimus thoracis muscle samples from 26 bull calves of 15 or 19 months of age (n=13 per age group) including the 14 samples already tested in the microarray study and 23 steers of 30 months of age. The expression data were subsequently related to meat tenderness score assessed by sensory analyses.

Materials and Methods

Animal and Muscle Samples

This study was conducted with 15- and 19-month-old Charolais bull calves and 30-month-old Charolais steers from an INRA experimental herd. All animals were weaned at 32 weeks and then kept in an open shed. Steers were castrated at 34 weeks of age. Young bulls were fed a complete pelleted diet distributed ad libitum with a limited amount of straw then slaughtered at 15 or 19 months, whereas steers were kept in an open shed until slaughter at 30 months of age. Longissimus thoracis muscle (LT) was excised from each animal within 10 min post-mortem. The samples were immediately frozen in liquid nitrogen and stored at −80° C. until analysis.

Sample Preparation

Total RNA was extracted from Longissimus thoracis muscle using Trizol reagent (Life technologies). A maximum of 100 µg of total RNA from each sample (n=49) was purified to eliminate contamination by genomic DNA using the NucleoSpin® RNA II kit (Macherey-Nagel GmbH & Co, Duren, Germany) as described in the manufacturer's protocol. RNA quality was assessed using an Agilent 2100 bioanalyzer (Agilent Technologies, Palo Alto, Calif.) and was quantified using a NanoDrop ND-1000 spectrophotometer (NanoDrop Technologie, Inc., USA).

Real-Time RT-PCR mRNA levels from all samples were assessed by real-time RT-PCR using DNAJA1 specific primer pair (Fw primer: AGGGTCGCCTAATCATTGAA or SEQ ID No 2, Rv primer: TCCTCGTATGCTTCTCCATTG or SEQ ID No 3) designed using Primer3 software and the LightCycler FastStart DNA master SYBR Green I kit (Roche Diagnostics GmbH, Mannheim, Germany) according to the manufacturer's instructions. A purified cDNA dilution was created for this gene to establish a standard curve to which results expressed in nanograms per micromole referred. The reaction was subjected to melting curve analysis to confirm single amplified products.

Sensory Assessment

LT steaks were vacuum packaged, aged at 4° C. for 14 days, and frozen. They were thawed rapidly under flowing water. On the following day they were grilled to a core temperature of 55° C. and immediately served to panellists. A total of 10-12 trained panellists were used in each session. They underwent 8-10 test sessions for training, during which they evaluated meats from different muscles, types of animals, and cooking processes. Once trained, they evaluated a maximum of eight meat samples, presented sequentially in each session. They scored initial tenderness and overall tenderness on 10-point scales: from 1 (tough) to 10 (tender). Meat samples from different bull calves and steers were randomly presented to the panellists. Each sample was tested once independently by each panellist. Scores were averaged over the different panellists for each animal.

Results and Discussion

DNAJA1 gene expression correlated with meat tenderness in bull calves

Figure 6:
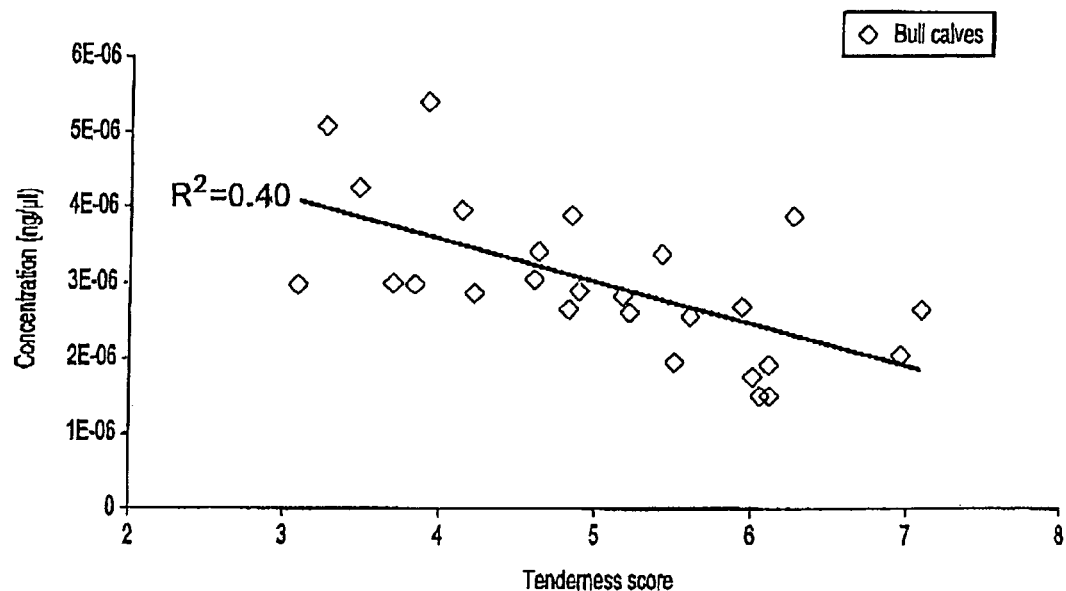
FIG. 6: Representation of the correlation between DNAJA1 gene expression level* and meat tenderness scores for 26 Charolais bull calves.

The real-time RT-PCR experiment confirmed the correlation found between DNAJA1 gene expression level and meat tenderness score not only for the fourteen 15- and 19-month-old bull calves as already obtained by microarray experiment, but also for all bull calves (n=26). The correlation coefficients were respectively |r|=0.69 for the 14 animals previously studied (Bernard et al., 2007) and |r|=0.63 for the 26 calves (FIG. 6).

DNAJA1 gene expression level was evaluated by real-time RT-PCR.

Within the subset of the 8 animals selected on the basis of extreme score values of meat tenderness, the correlation coefficient was |r|=0.74 (data not shown). Moreover, the down-regulation of DNAJA1 gene in muscles giving the tenderest meats was also validated.

Figure 7:
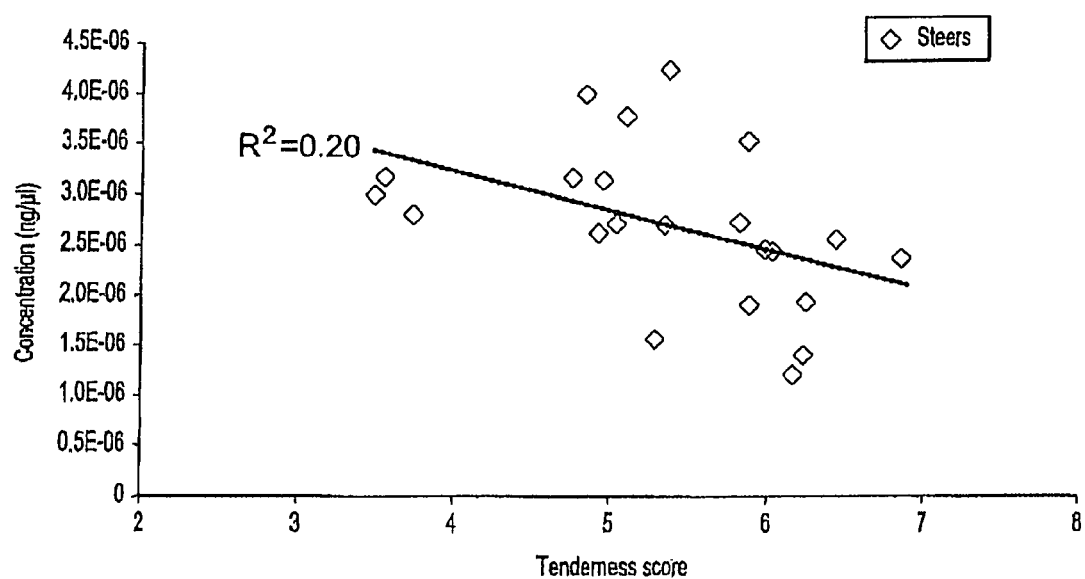
FIG. 7: Representation of the correlation between DNAJA1 gene expression level* and meat tenderness scores for 23 Charolais steers.

DNAJA1 gene expression correlated with meat tenderness in steers In steers, the DNAJA1 gene expression was also down-regulated in samples which gave the tenderest meats. The real-time RT-PCR results showed a lower correlation (|r|=0.45) between DNAJA1 gene expression level and meat tenderness score than in bull calves but it was significant (p<0.05) (FIG. 7).

DNAJA1 gene expression level was evaluated by real-time RT-PCR.

Moreover, there was a strong correlation (|r|=0.82) in samples resulting from the 6 animals selected for their extreme score value in meat tenderness (data not shown).

CONCLUSION

In conclusion, all results confirmed, on the one hand, the down-regulation of DNAJA1 gene expression in samples giving the tenderest meats and, on the other hand, the significant correlation between gene expression level and meat tenderness score in Charolais bull calves and steers. This suggests that DNAJA1 could be a good marker of meat tenderness in the Charolais breed since it alone is likely to explain at least 20% in tenderness variability with the new studied animals.

REFERENCES

Ansay M. Individualité musculaire chez le bovin: étude de l'équipment enzymatique de quelques muscles. *Ann Biol Anim Bioch Biophys* 14: 471-486, 1974.

Bai Q, McGillivray C, da Costa N, Dornan S, Evans G, Stear M J and Chang K C. Development of a porcine skeletal muscle cDNA microarray: analysis of differential transcript expression in phenotypically distinct muscles. *BMC Genomics* 4: 8, 2003.

Bartlett G R. Phosphorus assay in column chromatography. *J Biol Chem* 234: 466-468, 1959.

Benkel B, Kollers S, Fries R, Sazanov A, Yoshida E, Valle E, Davoren J and Hickey D. Characterization of the bovine ampkgammal gene. *Mamm Genome* 16: 194-200, 2005.

Bernard C, Degrelle S, Ollier S, Campion E, Cassar-Malek I, Charpigny G, Dhorne-Pollet S, Hue I, Hocquette J F, Le Provost F, Leroux C, Piumi F, Rolland G, Uzbekova S, Zalachas E and Martin P. A cDNA macro-array resource for gene expression profiling in ruminant tissues involved in reproduction and production (milk and beef) traits. *J Physiol Pharmacol* 56 Suppl 3: 215-224, 2005.

Bonnet M., Leroux C., Faulconnier Y., Hocquette J. F., Bocquier F., Martin P., Chilliard Y., 2000. Lipoprotein lipase activity and mRNA are up regulated by refeeding in adipose tissue and cardiac muscle of sheep. *J. Nutr.*, 130: 749-756, 2000.

Bourneuf E, Herault F, Chicault C, Carre W, Assaf S, Monnier A, Mottier S, Lagarrigue S, Douaire M, Mosser J and Diot C. Microarray analysis of differential gene expression in the liver of lean and fat chickens. *Gene* 372: 162-170, 2006.

Brazma A, Hingamp P, Quackenbush J, Sherlock G, Spellman P, Stoeckert C, Aach J, Ansorge W, Ball C A, Causton H C, Gaasterland T, Glenisson P, Holstege F C, Kim I F, Markowitz V, Matese J C, Parkinson H, Robinson A, Sarkans U, Schulze-Kremer S, Stewart J, Taylor R, Vilo J and Vingron M. Minimum information about a microarray experiment (MIAME)-toward standards for microarray data. *Nat Genet* 29: 365-371, 2001.

Briand M, Talmant A, Briand Y, Monin G and Durand R. Metabolic types of muscle in the sheep: I. Myosin ATPase, glycolytic, and mitochondrial enzyme activities. *Eur J Appl Physiol Occup Physiol* 46: 347-358, 1981.

Burnside J, Neiman P, Tang J, Basom R, Talbot R, Aronszajn M, Burt D and Delrow J. Development of a cDNA array for chicken gene expression analysis. *BMC Genomics* 6: 13, 2005.

Byrne K A, Wang Y H, Lehnert S A, Harper G S, McWilliam S M, Bruce H L and Reverter A. Gene expression profiling of muscle tissue in Brahman steers during nutritional restriction. *J Anim Sci* 83: 1-12, 2005.

Campo M M, Nute G R, Hughes S I, Enser M, Wood J D and Richardson R I. Flavour perception of oxidation in beef. *Meat Sci.* 72: 303-311, 2006.

Cassar-Malek I, Hocquette J F, Jurie C, Listrat A, Jailler R, Bauchart D, Briand Y and Picard B. Muscle-specific metabolic, histochemical and biochemical responses to a nutritionally induced discontinuous growth path. *Animal Sci.* 79: 49-59, 2004.

Cuvelier C, Cabaraux J F, Dufrasne I, Clinquart A, Hocquette J F, Istasse L and Hornick J L. Performance, slaughter characteristics and meat quality of young bulls from Belgian Blue, Limousin and Aberdeen Angus breeds fattened with a sugar-beet pulp or a cereal-based diet. *Animal Sci.* 82: 125-132, 2006.

Daniel S and Kim K H. Sp1 mediates glucose activation of the acetyl-CoA carboxylase promoter. *J Biol Chem* 271: 1385-1392, 1996.

Dieudonne M N, Pecquery R, Boumediene A, Leneveu M C and Giudicelli Y. Androgen receptors in human preadipocytes and adipocytes: regional specificities and regulation by sex steroids. *Am J Physiol* 274: C1645-C1652, 1998.

Eggen A and Hocquette J-F. Genomic approaches to economic trait loci and tissue expression profiling: application to muscle biochemistry and beef quality. *Meat Sci.* 66: 1-9, 2003.

Everts-van der Wind A, Larkin D M, Green C A, Elliott J S, Olmstead C A, Chiu R, Schein J E, Marra M A, Womack J E and Lewin H A. A high-resolution whole-genome cattle-human comparative map reveals details of mammalian chromosome evolution. *Proc Natl Acad Sci USA* 102: 18526-18531, 2005.

Folch J, Lees M and Slone-Stanley G H. A simple method for the isolation and purification of total lipids from animal tissues. *J Biol Chem* 226: 497-509, 1957.

Fu L and Liang J J. Enhanced stability of alpha B-crystallin in the presence of small heat shock protein Hsp27. *Biochem Biophys Res Commun* 302: 710-714, 2003.

Geay Y, Bauchart D, Hocquette J F and Culioli J. Effect of nutritional factors on biochemical, structural and metabolic characteristics of muscles in ruminants, consequences on dietetic value and sensorial qualities of meat. *Reprod Nutr Dev* 41: 1-26, 2001.

Goldfarb L G, Vicart P, Goebel H H and Dalakas M C. Desmin myopathy. *Brain* 127: 723-734, 2004.

Guay J, Lambert H, Gingras-Breton G, Lavoie J N, Huot J and Landry J. Regulation of actin filament dynamics by p38 map kinase-mediated phosphorylation of heat shock protein 27. *J Cell Sci* 110 (Pt 3): 357-368, 1997.

Hamilton S R, Stapleton D, O'Donnell J B Jr, Kung J T, Dalal S R, Kemp B E and Witters L A. An activating mutation in the gammal subunit of the AMP-activated protein kinase. *FEBS Lett* 500: 163-168, 2001.

Hocquette J F, Lehnert S A, Reecy J M, Cassar-Malek I and Martin P. cDNA arrays for gene expression profiling in cattle. *Proceedings of the 2$^{nd}$ International Conference on Cybernetics and Information Technologies, Systems and Applications, Orlando* (Fla., USA) 1: 3-5, 2005.

Hocquette J F, Richardson R I, Prache S, Medale F, Duffy G and Scollan N D. The future trends for research on quality and safety of animal products. *Ital J Anim Sci* 4: 49-72, 2005.

Hubbard S J, Grafham D V, Beattie K J, Overton I M, McLaren S R, Croning M D, Boardman P E, Bonfield J K, Burnside J, Davies R M, Farrell E R, Francis M D, Griffiths-Jones S, Humphray S J, Hyland C, Scott C E, Tang H, Taylor R G, Tickle C, Brown W R, Birney E, Rogers J and Wilson S A. Transcriptome analysis for the chicken based on 19,626 finished cDNA sequences and 485,337 expressed sequence tags. *Genome Res* 15: 174-183, 2005.

Klont R E, Brocks L and Eikelenboom G. Muscle Fibre Type and Meat Quality. *Meat Sci.* 49: S219-S229, 1998.

Koohmaraie M, Kent M P, Shackelford S D, Veiseth E and Wheeler T L. Meat tenderness and muscle growth: is there any relationship? *Meat Sci.* 62: 345-352, 2002.

Lametsch R, Karlsson A, Rosenvold K, Andersen H J, Roepstorff P and Bendixen E. Postmortem proteome changes of porcine muscle related to tenderness. *J Agric Food Chem* 51: 6992-6997, 2003.

Lamirault G, Gaborit N, Le Meur N, Chevalier C, Lande G, Demolombe S, Escande D, Nattel S, Leger J J and Steenman M. Gene expression profile associated with chronic atrial fibrillation and underlying valvular heart disease in man. *J Mol Cell Cardiol* 40: 173-184, 2006.

Le Meur N, Lamirault G, Bihouee A, Steenman M, Bedrine-Ferran H, Teusan R, Ramstein G and Leger J. A dynamic, web-accessible resource to process raw microarray scan data into consolidated gene expression values: importance of replication. *Nucleic Acids Res* 32: 5349-5358, 2004.

Lehnert S A, Wang Y H and Byrne K A. Development and application of a bovine cDNA microarray for expression profiling of muscle and adipose tissue. *Austr J Exp Agr* 44: 1127-1133, 2004.

Lehnert S A, Wang Y H, Tan S H and Reverter A. Gene expression-based approaches to beef quality research. *Australian Journal of Experimental Agriculture* 46: 165-172, 2006.

Leplaix-Charlat L, Durand D and Bauchart D. Effects of diets containing tallow and soybean oil with and without cholesterol on hepatic metabolism of lipids and lipoproteins in the preruminant calf. *J Dairy Sci* 79: 1826-1835, 1996.

Listrat A and Hocquette J F. Analytical limits of total and insoluble collagen content measurements and of type I and III collagen analysis by electrophoresis in bovine muscles. *Meat Sci.* 68: 127-136, 2004.

Listrat A, Rakadjiyski N, Jurie C, Picard B, Touraille C and Geay Y. Effect of the type of diet on muscle characteristics and meat palatability of growing Salers bulls. *Meat Meat Sci.* 53: 115-124, 1999.

Maltin C, Balcerzak D, Tilley R and Delday M. Determinants of meat quality: tenderness. *Proc Nutr Soc* 62: 337-347, 2003.

Milan D, Jeon J T, Looft C, Amarger V, Robic A, Thelander M, Rogel-Gaillard C, Paul S, Iannuccelli N, Rask L, Ronne H, Lundstrom K, Reinsch N, Gellin J, Kalm E, Roy P L, Chardon P and Andersson L. A mutation in PRKAG3 associated with excess glycogen content in pig skeletal muscle. *Science* 288: 1248-1251, 2000.

Monson F, Sanudo C and Sierra I. Influence of cattle breed and ageing time on textural meat quality. *Meat Meat Sci.* 68: 595-602, 2004.

Monson F, Sanudo C and Sierra I. Influence of breed and ageing time on the sensory meat quality and consumer acceptability in intensively reared beef. *Meat Meat Sci.* 71: 471-479, 2005.

Morzel M, Chambon C, Hamelin M, Santé-Lhoutellier V, Sayd T and Monin G. Proteome changes during pork meat ageing following use of two different pre-slaughter handling procedures. *Meat Meat Sci.* 67: 689-696, 2004.

Plastow G S, Carrion D, Gil M, Garcia-Regueiro J A, Font i Furnols M, Gispert M, Oliver M A, Velarde A, Guardia M D and Hortos M. Quality pork genes and meat production. *Meat Meat Sci.* 3: 409-421, 2005.

Potts J K, Echtemkamp S E, Smith T P and Reecy J M. Characterization of gene expression in double-muscled and normal-muscled bovine embryos. *Anim Genet* 34: 438-444, 2003.

Renand G, Picard B, Touraille C, Berge P and Lepetit J. Relationships between muscle characteristics and meat quality traits of young Charolais bulls. *Meat Meat Sci.* 59: 49-60, 2001.

Robelin J and Geay Y. Estimation de la composition des carcasses de jeunes bovins à partir de la composition d'un morceau monocostal prélevé au niveau de la 11$^{eme}$ côte. *Ann Zoot* 24: 391-402, 1975.

Sami A S, Augustini C and Schwarz F J. Effects of feeding intensity and time on feed on performance, carcass characteristics and meat quality of Simmental bulls. *Meat Meat Sci.* 67: 195-201, 2004.

Sanudo C, Macie E S, Olleta J L, Villarroel M, Panea B and Alberti P. The effects of slaughter weight, breed type and ageing time on beef meat quality using two different texture devices. *Meat Science* 66: 925-932, 2004.

Smih F, Rouet P, Lucas S, Mairal A, Sengenes C, Lafontan M, Vaulont S, Casado M and Langin D. Transcriptional regulation of adipocyte hormone-sensitive lipase by glucose. *Diabetes* 51: 293-300, 2002.

Sturn A, Quackenbush J and Trajanoski Z. Genesis: cluster analysis of microarray data. *Bioinformatics* 18: 207-208, 2002.

Sudre K, Cassar-Malek I, Listrat A, Ueda Y, Leroux C, Jurie C, Auffray C, Renand G, Martin P and Hocquette J F. Biochemical and transcriptomic analyses of two bovine skeletal muscles in Charolais bulls divergently selected for muscle growth. *Meat Sci.* 70: 267-277, 2005.

Sudre K, Leroux C, Cassar-Malek I, Hocquette J F and Martin P. A collection of bovine cDNA probes for gene expression profiling in muscle. *Mol Cell Probes* 19: 61-70, 2005.

Sudre K, Leroux C, Pietu G, Cassar-Malek I, Petit E, Listrat A, Auffray C, Picard B, Martin P and Hocquette J F. Transcriptome analysis of two bovine muscles during ontogenesis. *J Biochem* (Tokyo) 133: 745-756, 2003.

Thomas P D, Kejariwal A, Campbell M J, Mi H, Diemer K, Guo N, Ladunga I, Ulitsky-Lazareva B, Muruganujan A, Rabkin S, Vandergriff J A and Doremieux O. PANTHER: a browsable database of gene products organized by biological function, using curated protein family and subfamily classification. *Nucleic Acids Res* 31: 334-341, 2003.

Tusher V G, Tibshirani R and Chu G. Significance analysis of microarrays applied to the ionizing radiation response. *Proc Natl Acad Sci USA* 98: 5116-5121, 2001.

Veiseth E and Koohmaraie M. Beef tenderness: significance of the calpain proteolytic system. Indicators of milk and beef quality, *EAAP Publication* 112, *Wageningen Academic Publishers, Wageningen, The Netherlands* 111-126, 2005.

Wang X, Klevitsky R, Huang W, Glasford J, Li F and Robbins J. AlphaB-crystallin modulates protein aggregation of abnormal desmin. *Circ Res* 93: 998-1005, 2003.

Wang Y H, Byrne K A, Reverter A, Harper G S, Taniguchi M, McWilliam S M, Mannen H, Oyama K and Lehnert S A. Transcriptional profiling of skeletal muscle tissue from two breeds of cattle. *Mamm Genome* 16: 201-210, 2005.

Wang Y H, Reverter A, Mannen H, Taniguchi M, Harper G S, Oyama K, Byrne K A, Oka A, Tsuji S and Lehnert S A. Transcriptional profiling of muscle tissue in growing Japanese Black cattle to identify genes involved with the development of intramuscular fat. *Aust J Exp Agr* 45: 809-820, 2005.

Wood J D, Richardson R I, Nute G R, Fisher A V, Campo M M, Kasapidou E, Sheard P R and Enser M. Effects of fatty acids on meat quality: a review. *Meat Sci.* 66: 21-32, 2003.

Zhu Q and Liao K. Differential expression of the adipocyte amino acid transporter is transactivated by SP1 and SP3 during the 3T3-L1 preadipocyte differentiation process. *Biochem Biophys Res Commun* 271: 100-106, 2000.

Bernard C, Cassar-Malek I, Le Cunff M., Dubroeucq H., Renand G., Hocquette J F. New indicators of beef sensory quality revealed by expression of specific genes. *J Agric Food Chem* 2007, 55, 5229-5237.

---

The invention claimed is:

1. A method for determining tenderness of meat of a bovine animal, comprising determining, in a biological sample, the level of expression of a nucleotide sequence which encodes the protein encoded by the nucleotide sequence set forth in SEQ ID NO: 1, in a bovine animal, and correlating said level of expression to degree of tenderness of the meat of said bovine animal.

2. The method of claim 1, comprising determining said level of expression at slaughter of said bovine animal.

3. The method of claim 1, comprising determining said level of expression in a muscle of said bovine animal.

4. The method of claim 1, further comprising comparing level of expression of said nucleotide sequence to level of expression of a control nucleotide sequence.

5. The method of claim 4, wherein said control nucleotide sequence is set forth in SEQ ID NO: 6.

6. The method of claim 3, further comprising assaying a series of different muscles.

7. The method of claim 1, comprising determining said expression level by contacting said nucleotide sequence with an oligonucleotide sequence consisting of from 5 to 50 consecutive nucleotides of the nucleotide sequence being measured.

8. The method of claim 7, wherein said oligonucleotide sequence consists of from 10 to 30 consecutive nucleotides of the nucleotide sequence being measured.

9. The method of claim 7, wherein said oligonucleotide sequence comprises SEQ ID NO: 2 or SEQ ID NO: 3.

10. The method of claim 7, wherein said oligonucleotide sequence consists of SEQ ID NO: 2 or SEQ ID NO: 3.

11. The method of claim 4, further comprising determining level of expression of a control nucleotide sequence by contacting said control nucleotide sequence with an oligonucleotide sequence consisting of from 5 to 50 consecutive nucleotides of said control nucleotide sequence.

12. The method of claim 11, wherein said oligonucleotide sequence consists of from 10 to 30 consecutive nucleotides of said control nucleotide sequence.

13. The method of claim 11, wherein said oligonucleotide sequence comprises SEQ ID NO: 7 or SEQ ID NO: 8.

14. The method of claim 11, wherein said oligonucleotide sequence consists of SEQ ID NO: 7 or SEQ ID NO: 8.

15. The method of claim 1, further comprising:
(a) purifying total RNA from a muscle sample of said bovine animal,
(b) reverse transcribing said total RNA to cDNA,
(c) contacting said cDNA with two oligonucleotide primers consisting of from 5 to 50 consecutive nucleotides of the nucleotide sequence to be identified,
(d) subjecting said cDNA to polymerase chain reaction,
(e) quantifying any amplified nucleic acid molecule produced in (d), and
(f) comparing amount of said amplified nucleic acid molecule to amount of an amplified control nucleic acid sequence, as a determination of tenderness of meat.

16. The method of claim 15, wherein said oligonucleotide primers consist of from 10 to 30 consecutive nucleotides of said nucleotide sequence.

17. The method of claim 2, further comprising real-time RT-PCR.

18. The method of claim 17, further comprising labelling said cDNA with a detectable label after step (b).

19. The method of claim 1, further comprising:
(a) purifying total protein from a muscle sample of said bovine animal,
(b) contacting said total protein with an antibody which specifically binds to the protein encoded by the nucleotide sequence, and
(c) detecting level of binding as a determination of tenderness of said meat.

20. The method of claim 19, wherein said antibody is labelled with a detectable label.

* * * * *

SEQUENCE LISTING

```
<160> NUMBER OF SEQ ID NOS: 31

<210> SEQ ID NO 1
<211> LENGTH: 1449
<212> TYPE: DNA
<213> ORGANISM: Bos taurus

<400> SEQUENCE: 1
aacgctcggt gaaaggcgga ggagcggcgg ctgcccgagc tgcgcacagc aacgcgctcc      60
ttcccgctcc cccacaccgg catcggcccg ctcaccggct gtaaaaaatg gtgaaagaaa     120
ccacttacta tgatgttttg ggggtcaaac ccaatgccac ccaagaagaa ttgaaaaagg     180
cttacaggaa actggccttg aagtaccacc ctgataagaa tccaaatgaa ggcgagaagt     240
ttaaacagat ttctcaagct tacgaagtgc tctctgatgc aaagaaaagg gagttatatg     300
```

```
acaaaggagg agaacaggca attaaagaag gtggagcagg tggtggtttt ggctccccca      360
tggacatctt tgatatgttt ttcggaggag gaggcaggat gcacagagag aggagaggta      420
aaaacgttgt ccatcaactt acagtaactt tagaagattt atataatggt gcaacaagaa      480
aactagctct gcaaaagaat gtgatttgtg acaaatgtga aggccgaggt ggtaaaaaag      540
gagcagtaga atgctgtccc aattgccgag gtactggaat gcaaataaga attcatcaga      600
taggacctgg aatggttcag caaattcagt ctgtctgcat ggagtgccat tgtcatgggg      660
agcggatcac ccctaaagat agatgtaaaa gctgcaatgg aaggaagata gttcgagaaa      720
agaaaattct agaagttcat attgacaaag gcatgaaaga tggccagaag ataacattcc      780
atggtgaagg agaccaagaa ccaggactgg agccgggaga tattatcatt gttttagatc      840
agaaggacca tgctgttttt actcgacgag gagaagacct tttcatgtgt atggacatac      900
agctggttga ggcattgtgt ggcttccaaa agccaatatc tactcttgac aaccgaacca      960
tagtcatcac ttctcatcca ggtcaaattg tcaagcatgg agatatcaag tgtgtgctaa     1020
atgaaggcat gccaatttat cgtaggccat acgaaaaggg tcgcctaatc attgaattta     1080
aggtaaactt tcctgagaat ggctttctct ctcctgataa actctctttg ctggaaaaac     1140
ttctgcctga gaggaaggaa gtagaagaga ctgatgaaat ggaccaggta gaattagtgg     1200
actttgatcc aaatcaggaa agacggcgcc attacaatgg agaagcatac gaggatgatg     1260
aacatcatcc tcggggtggt gttcagtgtc agacctctta gtagggcctg tgaacaacac     1320
tcactgctgg tgttttatt gcagtagtga ttgagtgaag gactataatc atatgctcac     1380
tacttgcttt tgttttaata ttcaactata gtagtgttta aagttaaat gaagaataaa     1440 ctcaaatat                                                             1449

<210> SEQ ID NO 2
<211> LENGTH: 20
<212> TYPE: DNA
<213> ORGANISM: Bos taurus

<400> SEQUENCE: 2
agggtcgcct aatcattgaa                                                   20

<210> SEQ ID NO 3
<211> LENGTH: 21
<212> TYPE: DNA
<213> ORGANISM: Bos taurus

<400> SEQUENCE: 3
caatggagaa gcatacgagg a                                                 21

<210> SEQ ID NO 4
<211> LENGTH: 50
<212> TYPE: DNA
<213> ORGANISM: Bos taurus

<400> SEQUENCE: 4
agaatggctt tctctctcct gataaactct ctttgctgga aaaacttctg                  50

<210> SEQ ID NO 5
<211> LENGTH: 158
<212> TYPE: DNA
<213> ORGANISM: Bos taurus

<400> SEQUENCE: 5
tttaaggtaa actttcctga gaatggcttt ctctctcctg ataaactctc tttgctggaa       60
```

```
aaacttctgc ctgagaggaa ggaagtagaa gagactgatg aaatggacca ggtagaatta    120
gtggactttg atccaaatca ggaaagacgg cgccatta                            158

<210> SEQ ID NO 6
<211> LENGTH: 854
<212> TYPE: DNA
<213> ORGANISM: Bos taurus

<400> SEQUENCE: 6
tttcggagcg gaacatgaag atcctattcg tcgccgccct ggttgtgggc tccgtgttct     60
tcctgctgtt gcctggacca tccgcggccg atgagaagaa gaaggggccc aaagtcactg    120
tcaaggtgta ctttgacctg cgaattggag atgaagatat aggccgggtg gtcatcggtc    180
tctttggaaa gactgttcca aaaacagtgg ataattttgt ggccttggct acaggagaga    240
aaggatttgg ctacaaagac agcaaattcc atcgtgtgat caaggacttc atgatccagg    300
gtggagattt cacccgggga gacggcactg gaggtaagag catctacggt gaacgcttcc    360
ccgatgagaa cttcaagctt aaacactatg gcccggctg  ggtgagcatg gccaacgcgg    420
gcaaagacac caacggctcc cagttcttca tcacgacagt caagactgcc tggctagatg    480
gcaagcacgt aggtttcggc aaagttctag agggcatgga tgtagtacgg aaggtagaga    540
gcaccaagac tgacggtcgg acaagcctc  tgaaggacgt gacgatcgca gactgcggca    600
agatcgaggt ggagaagccc tttgccattg ccaaggaata gggccccagg gacctcttcc    660
ctttgagcaa ctgtctgtgt ggccctgtcg tcctcccagg ggtgaagata gcccgccaca    720
gggctccgtg cgcgctggcc ccagggctgg catcttacag ggcgggcccc tcccctccat    780
tccatgggcc cagttttgta acaaactcct accaacactg accaataaaa aaatggtgt     840 tttttttta aaaa                                                       854

<210> SEQ ID NO 7
<211> LENGTH: 20
<212> TYPE: DNA
<213> ORGANISM: Bos taurus

<400> SEQUENCE: 7
ggtcatcggt ctctttggaa                                                 20

<210> SEQ ID NO 8
<211> LENGTH: 20
<212> TYPE: DNA
<213> ORGANISM: Bos taurus

<400> SEQUENCE: 8
agacggcact ggaggtaaga                                                 20

<210> SEQ ID NO 9
<211> LENGTH: 20
<212> TYPE: DNA
<213> ORGANISM: Bos taurus

<400> SEQUENCE: 9
cttccacgtc tccagcaagt                                                 20

<210> SEQ ID NO 10
<211> LENGTH: 20
<212> TYPE: DNA
<213> ORGANISM: Bos taurus

<400> SEQUENCE: 10
```
gccgatgata gcaaccctaa	20

<210> SEQ ID NO 11
<211> LENGTH: 20
<212> TYPE: DNA
<213> ORGANISM: Bos taurus

<400> SEQUENCE: 11
caagatgtcg ttccccaagt	20

<210> SEQ ID NO 12
<211> LENGTH: 20
<212> TYPE: DNA
<213> ORGANISM: Bos taurus

<400> SEQUENCE: 12
gttgcatcaa agtcgcagaa	20

<210> SEQ ID NO 13
<211> LENGTH: 20
<212> TYPE: DNA
<213> ORGANISM: Bos taurus

<400> SEQUENCE: 13
caccaacctg tccaagttcc	20

<210> SEQ ID NO 14
<211> LENGTH: 20
<212> TYPE: DNA
<213> ORGANISM: Bos taurus

<400> SEQUENCE: 14
ctggaggagg agctgaagaa	20

<210> SEQ ID NO 15
<211> LENGTH: 20
<212> TYPE: DNA
<213> ORGANISM: Bos taurus

<400> SEQUENCE: 15
acttggctgg cagcttttta	20

<210> SEQ ID NO 16
<211> LENGTH: 20
<212> TYPE: DNA
<213> ORGANISM: Bos taurus

<400> SEQUENCE: 16
tctgcctgtc gatgtcactc	20

<210> SEQ ID NO 17
<211> LENGTH: 20
<212> TYPE: DNA
<213> ORGANISM: Bos taurus

<400> SEQUENCE: 17
atgcggaaag tcggtctatg	20

<210> SEQ ID NO 18
<211> LENGTH: 20
<212> TYPE: DNA
<213> ORGANISM: Bos taurus

<400> SEQUENCE: 18

-continued cgccattact tcatccctgt            20

<210> SEQ ID NO 19
<211> LENGTH: 20
<212> TYPE: DNA
<213> ORGANISM: Bos taurus

<400> SEQUENCE: 19
cgttgcttca ctcgcaaata            20

<210> SEQ ID NO 20
<211> LENGTH: 20
<212> TYPE: DNA
<213> ORGANISM: Bos taurus

<400> SEQUENCE: 20
ttccggagat gttcttggag            20

<210> SEQ ID NO 21
<211> LENGTH: 20
<212> TYPE: DNA
<213> ORGANISM: Bos taurus

<400> SEQUENCE: 21
gcttgcttgg ttctctggtc            20

<210> SEQ ID NO 22
<211> LENGTH: 20
<212> TYPE: DNA
<213> ORGANISM: Bos taurus

<400> SEQUENCE: 22
ccaaggcagg atcttcgata            20

<210> SEQ ID NO 23
<211> LENGTH: 20
<212> TYPE: DNA
<213> ORGANISM: Bos taurus

<400> SEQUENCE: 23
gcttcacagg ggagtttgaa            20

<210> SEQ ID NO 24
<211> LENGTH: 20
<212> TYPE: DNA
<213> ORGANISM: Bos taurus

<400> SEQUENCE: 24
actgggagct tcagttgcac            20

<210> SEQ ID NO 25
<211> LENGTH: 20
<212> TYPE: DNA
<213> ORGANISM: Bos taurus

<400> SEQUENCE: 25
cagcttggct accgatctct            20

<210> SEQ ID NO 26
<211> LENGTH: 20
<212> TYPE: DNA
<213> ORGANISM: Bos taurus

<400> SEQUENCE: 26

```
actgggattg cagcagaact                                               20

<210> SEQ ID NO 27
<211> LENGTH: 18
<212> TYPE: DNA
<213> ORGANISM: Bos taurus

<400> SEQUENCE: 27
gttgcgggcc acaaactt                                                 18

<210> SEQ ID NO 28
<211> LENGTH: 21
<212> TYPE: DNA
<213> ORGANISM: Bos taurus

<400> SEQUENCE: 28
tcctcgtatg cttctccatt g                                             21

<210> SEQ ID NO 29
<211> LENGTH: 20
<212> TYPE: DNA
<213> ORGANISM: Bos taurus

<400> SEQUENCE: 29
acctgtaggg ccgaagtttt                                               20

<210> SEQ ID NO 30
<211> LENGTH: 20
<212> TYPE: DNA
<213> ORGANISM: Bos taurus

<400> SEQUENCE: 30
tcactggtgg ggaactttc                                                20

<210> SEQ ID NO 31
<211> LENGTH: 20
<212> TYPE: DNA
<213> ORGANISM: Bos taurus

<400> SEQUENCE: 31
tacttgtttc cggctgttcg                                               20
```